US008759307B2

(12) United States Patent
Stein et al.

(10) Patent No.: US 8,759,307 B2

(45) Date of Patent: Jun. 24, 2014

(54) OLIGONUCLEOTIDE COMPOUND AND METHOD FOR TREATING NIDOVIRUS INFECTIONS

(75) Inventors: David A. Stein, Corvallis, OR (US); Richard K. Bestwick, Corvallis, OR (US); Patrick L. Iversen, Corvallis, OR (US); Benjamin Neuman, Encinitas, CA (US); Michael Buchmeier, Encinitas, CA (US); Dwight D. Weller, Corvallis, OR (US)

(73) Assignees: Sarepta Therapeutics, Inc., Corvallis, OR (US); The Scripps Research Institute, La Jolla, CA (US)

( * ) Notice: Subject to any disclaimer, the term of this patent is extended or adjusted under 35 U.S.C. 154(b) by 1101 days.

(21) Appl. No.: 12/109,856

(22) Filed: Apr. 25, 2008

(65) Prior Publication Data

US 2009/0012280 A1 Jan. 8, 2009

Related U.S. Application Data

(60) Division of application No. 11/432,155, filed on May 10, 2006, now abandoned, which is a continuation-in-part of application No. 11/022,358, filed on Dec. 22, 2004, now abandoned.

(60) Provisional application No. 60/532,701, filed on Dec. 24, 2003.

(51) Int. Cl.

| | |
|---|---|
| ***A61K 48/00*** | (2006.01) |
| ***C07H 21/04*** | (2006.01) |
| ***C07H 21/02*** | (2006.01) |
| ***C12N 7/00*** | (2006.01) |

(52) U.S. Cl.

USPC ............................ 514/44; 536/23.1; 536/24.5

(58) Field of Classification Search

CPC ....................................................... C12N 15/11

USPC ........................ 514/44; 536/23.1, 24.5, 235.1

See application file for complete search history.

(56) References Cited

U.S. PATENT DOCUMENTS

| | | | | |
|---|---|---|---|---|
| 5,185,444 | A | 2/1993 | Summerton et al. | |
| 5,892,023 | A * | 4/1999 | Pirotzky et al. | 536/24.5 |
| 6,365,351 | B1 | 4/2002 | Iversen | |
| 6,677,153 | B2 | 1/2004 | Iversen | |
| 6,784,291 | B2 | 8/2004 | Iversen et al. | |
| 6,828,105 | B2 | 12/2004 | Stein et al. | |
| 6,841,542 | B2 | 1/2005 | Bartelmez et al. | |
| 7,049,431 | B2 | 5/2006 | Iversen et al. | |
| 7,094,765 | B1 | 8/2006 | Iversen et al. | |
| 7,468,418 | B2 * | 12/2008 | Iversen et al. | 530/300 |
| 7,943,762 | B2 | 5/2011 | Weller et al. | 536/31 |
| 2003/0224353 | A1 | 12/2003 | Stein et al. | |
| 2006/0257852 | A1 | 11/2006 | Rappuoli et al. | |
| 2006/0269911 | A1 | 11/2006 | Iversen et al. | 435/5 |
| 2006/0287268 | A1 | 12/2006 | Iversen et al. | 514/44 |
| 2007/0021362 | A1 | 1/2007 | Geller et al. | 514/44 |
| 2007/0265214 | A1 | 11/2007 | Stein et al. | 514/44 |
| 2009/0088562 | A1 | 4/2009 | Weller et al. | 536/24.5 |

FOREIGN PATENT DOCUMENTS

| | | |
|---|---|---|
| WO | WO2005/000234 A1 | 1/2005 |
| WO | WO2005/013905 A1 | 2/2005 |

OTHER PUBLICATIONS

Moulton et al Bioconjug Chem. Mar.-Apr. 2004;15(2):290-9. Cellular uptake of antisense morpholino oligomers conjugated to arginine-rich peptides.*

Moulton et al Antisense Nucleic Acid Drug Dev. Feb. 2003;13(1):31-43. HIV Tat peptide enhances cellular delivery of antisense morpholino oligomers.*

Geller et al., Inhibition of Gene Expression in *Escherichia coli* by Antisense Phosphorodiamidate Morpholino Oligomers Antimicrobial Agents and Chemotherapy, Oct. 2003, p. 3233-3239, vol. 47, No. 10.*

Agrawal, S., S. H. Mayrand, et al. (1990). "Site-specific excision from RNA by RNase H and mixed-phosphate-backbone oligodeoxynucleotides." *Proc Natl Acad Sci U S A*, 87(4):1401-5.

Agrawal et al., "Antisense therapeutics: is it as simple as complementary base recognition?", *Molecular Med. Today*, 6:72-81 (2000).

Allende, R., T. L. Lewis, et al. (1999). "North American and European porcine reproductive and respiratory syndrome viruses differ in non-structural protein coding regions." *J Gen Virol.*, 80( Pt 2):307-15.

Bailey, C. P., J. M. Dagle et al., (1998). "Cationic oligonucleotides can mediate specific inhibition of gene expression in *Xenopus* oocytes." *Nucleic Acids Res.*, 26(21):4860-7.

Barawkar, D. A. and T. C. Bruice, (1998). "Synthesis, biophysical properties, and nuclease resistance properties of mixed backbone oligodeoxynucleotides containing cationic internucleoside guanidinium linkages: deoxynucleic guanidine/DNA chimeras." *Proc Nat Acad Sci U S A*, 95(19):11047-52.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res.*, 22(20):4187-94.

Bonham, M. A., S. Brown, et al. (1995). "An assessment of the antisense properties of RNase H-competent and steric-blocking oligomers." *Nucleic Acids Res.* 23(7): 1197-203.

Boudvillain, M., M. Guerin, et al. (1997). "Transplatin-modified oligo(2'-O-methyl ribonucleotide)s: a new tool for selective modulation of gene expression." *Biochemistry*, 36(10): 2925-31.

(Continued)

*Primary Examiner* — Maria Leavitt

(74) *Attorney, Agent, or Firm* — Seed IP Law Group PLLC

(57) ABSTRACT

A method and oligonucleotide compound for inhibiting replication of a nidovirus in virus-infected animal cells are disclosed. The compound (i) has a nuclease-resistant backbone, (ii) is capable of uptake by the infected cells, (iii) contains between 8-25 nucleotide bases, and (iv) has a sequence capable of disrupting base pairing between the transcriptional regulatory sequences in the 5' leader region of the positive-strand viral genome and negative-strand 3' subgenomic region. In practicing the method, infected cells are exposed to the compound in an amount effective to inhibit viral replication.

8 Claims, 11 Drawing Sheets

(56) References Cited

OTHER PUBLICATIONS

Dagle, J. M., J. L. Littig, et al. (2000). "Targeted elimination of zygotic messages in *Xenopus laevis* embryos by modified oligonucleotides possessing terminal cationic linkages." *Nucleic Acids Res.*, 28(10): 2153-7.

de Vries, A. A. F., M. C. Horzinek, et al. (1997). "The Genome Organization of the Nidovirales: Similarities and Differences between Arteri-, Toro-, and Coronaviruses* 1." *Seminars in Virology*, 8(1): 33-47.

Ding, D., S. M. Grayaznov, et al. (1996). "An oligodeoxyribonucleotide N3'.fwdarw.P5' phosphoramidate duplex forms an A-type helix in solution." *Nucleic Acids Res.*, 24(2):354-60.

Felgner, P. L., T. R. Gadek, et al. (1987). "Lipofection: a highly efficient, lipid-mediated DNA-transfection procedure." *Proc Natl Acad Sci U S A*, 84(21):7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc* [Perkin 1] 0(14):1684-6.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev.*, 8(2):103-11.

Guan, Y., B. J. Zheng, et al. (2003). "Isolation and Characterization of Viruses Related to the SARS Coronavirus from Animals in Southern China." *Science*, 302:276-278.

Hedges et al., (2004). *J. Gen. Virol.*, 85(Part 2):379-390.

Homes et al., (2003). "The SARS Coronavirus: A Postgnomic Era", *Science*, pp. 1377-1378.

Lai, M. M. and D. Cavanagh (1997). "The molecular biology of coronaviruses." *Adv Virus Res.*, 48: 1-100.

Lesnikowski, Z. J., M. Jaworska, et al. (1990). "Octa(thymidine methanephosphonates) of partially defined stereochemistry: synthesis and effect of chirality at phosphorus on binding to pentadecadeoxyriboadenylic acid." *Nucleic Acids Res.*, 18(8):2109-15.

Linkletter, B. A. and Bruice, T.C., "Solid-phase synthesis of positively charged deoxynucleic guanidine (DNG) modified oligonucleotides containing neutral urea linkages: Effect of charge deletions on binding and fidelity." *Bioorg. Med. Chem.* 8(11):1893-1901 (2000).

Lu et al., (2004). "Attenuation of SARS coronavirus by a short hairpin RNA expression plasmid targeting RNA-dependent RNA polymerase", *Virology*, 324(1):84-89.

Micklefield, J., "Backbone modification of nucleic acids: synthesis, structure and therapeutic applications." *Curr Med Chem*, 8(10):1157-79 (2001).

NCBI Accession No. AY274119, SARS Coronavirus Tor2, complete genome, p. 1-2.

Marra, M. A., S. J. M. Jones, et al. (2003). "The Genome Sequence of the SARS-Associated Coronavirus." *Science*, 300(5624):1399-1404.

McCaffrey A.P. et al. (2003). "A potent and Specific Morpholino Antisense Inhibitor of Hepatitis C Translation in Mice", *Hepatology*, 38(2):503-508.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl)carbonate, and 3'-(5-fluoro-2'-deoxyuridinyl) 5'-thymidinyl carbonate." *J Med Chem.*, 12(1):154-7.

Moulton, H. M. and J. D. Moulton (2003). "Peptide-assisted delivery of steric-blocking antisense oligomers." *Curr Opin Mol Ther.*, 5(2):123-32.

Neuman et al., (2004). "Antisense morpholino-oligomers directed against the 5' end of the genome inhibit coronavirus proliferation and growth", *Journal of Virology*, 48(11):5891-5899.

Pasternak, A. O., E. van den Born, et al. (2001). "Sequence requirements for RNA strand transfer during nidovirus discontinuous subgenomic RNA synthesis." *Embo J* 20(24):7220-8.

Pasternak, A. O., E. van den Born, et al. (2003). "The Stability of the Duplex between Sense and Antisense Transcription-Regulating Sequences Is a Crucial Factor in Arterivirus Subgenomic mRNA Synthesis." *J. Virol.*, 77(2):1175-1183.

Pasternak, A. O., W. J. Spaan, et al. (2004). "Regulation of relative abundance of arterivirus subgenomic mRNAs." *J Virol.*, 78(15):8102-13.

Peiris, J. S., K. Y. Yuen, et al. (2003). "The severe acute respiratory syndrome." *N Engl J Med.*, 349(25):2431-41.

Rota, P. A., M. S. Oberste, et al. (2003). "Characterization of a novel coronavirus associated with severe acute respiratory syndrome." *Science*, 300(5624):1394-9.

Savarinio et al., (2006). "Potential Therapies for Coronaviruses", Expert. Opin. Ther., 1269-1288.

Sawicki, S. G. and D. L. Sawicki (1998). "A new model for coronavirus transcription." *Adv Exp Med Biol.*, 440:215-9.

Schiavone, N., et al., (2004). "Antisense oligonucleotide drug design", *Current Pharmaceutical Design*, 10(7):769-784.

Stein, D., E. Foster, et al. (1997). "A specificity comparison of four antisense types: morpholino, 2'-O-methyl RNA, DNA, and phosphorothioate DNA." *Antisense Nucleic Acid Drug Dev.*, 7(3):151-7.

Summerton, J. and D. Weller (1997). "Morpholino antisense oligomers: design, preparation, and properties." *Antisense Nucleic Acid Drug Dev.*, 7(3):187-95.

Thiel, V. et al., (Jun. 11, 1993), Genbank Accession No. AY291315, "SARS Coronavirus Frankfurt 1 Complete Genome", [retrieved Mar. 23, 2005].

Thiel, V., K. A. Ivanov, et al. (2003). "Mechanisms and enzymes involved in SARS coronavirus genome expression." *J Gen Virol.*, 84(Pt 9): 2305-15.

Toulme, J. J., R. L. Tinevez, et al. (1996). "Targeting RNA structures by antisense oligonucleotides." *Biochimie*, 78(7): 663-73.

Van Den Born, et al. (2004). "Secondary structure and function of the 5'-proximal region of the equine arteritis virus RNA genome." *RNA*, 10(3):424-437.

Wang et al., (2004). "Inhibition of severe acute respiratory syndrome virus replication by small interfering RNAs in mammalian cells", 78(14):7523-7527.

Zeng, L., E. K. Godeny, et al. (1995). "Analysis of simian hemorrhagic fever virus (SHFV) subgenomic RNAs, junction sequences, and 5' leader." *Virology*, 207(2): 543-8.

Zhang et al., (2003). Inhibiting severe acute respiratory syndrome-associated coronavirus by small interfering RNA, *Chinese Medical Journal*, 116(8):1262-1264.

Zheng et al., (2004). "Prophylactic and therapeutic effects of small interfering RNA targeting SARS-coronavirus", *Antiviral Therapy*, 9(3):365-374.

Ziebuhr, J., E. J. Snijder, et al. (2000). "Virus-encoded proteinases and proteolytic processing in the Nidovirales." *J Gen Virol.*, 81(4):853-879.

* cited by examiner

OLIGONUCLEOTIDE COMPOUND AND METHOD FOR TREATING NIDOVIRUS INFECTIONS

This application is a divisional of U.S. application Ser. No. 11/432,155 filed May 10, 2006, now abandoned, which is a continuation-in-part of U.S. application Ser. No. 11/022,358 filed Dec. 22, 2004, now abandoned, which claims the benefit of priority of U.S. Application No. 60/532,701 filed Dec. 24, 2003, now abandoned. All applications are incorporated in their entirety herein by reference.

A portion of the work described herein was supported by grant numbers NS 41219, AI 43103, AI 25913 from the National Institutes of Health, and HHSN266200400058C from Health and Human Services, The United States Government has certain rights in this invention.

FIELD OF THE INVENTION

This invention relates to an oligonucleotide analog for use in treating in animals a coronavirus infection or, more generally, an infection by a member of the Nidovirales order, to an antiviral method employing the analog, and to a method for monitoring binding of the analog to a viral genome target site.

REFERENCES

Agrawal, S., S. H. Mayrand, et al. (1990). "Site-specific excision from RNA by RNase H and mixed-phosphate-backbone oligodeoxynucleotides." *Proc Natl Acad Sci USA* 87(4): 1401-5.

Allende, R., T. L. Lewis, et al. (1999). "North American and European porcine reproductive and respiratory syndrome viruses differ in non-structural protein coding regions." *J Gen Virol* 80 (Pt 2): 307-15.

Balasuriya, U. B., J. F. Hedges, et al. (2004). "Genetic characterization of equine arteritis virus during persistent infection of stallions." *J Gen Virol* 85(Pt 2): 379-90.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res* 22(20): 4187-94.

Bonham, M. A., S. Brown, et al. (1995). "An assessment of the antisense properties of RNase H-competent and steric-blocking oligomers." *Nucleic Acids Res* 23(7): 1197-203.

Boudvillain, M., M. Guerin, et al. (1997). "Transplatin-modified oligo(2'-O-methyl ribonucleotide)s: a new tool for selective modulation of gene expression." *Biochemistry* 36(10): 2925-31.

Dagle, J. M., J. L. Littig, et al. (2000). "Targeted elimination of zygotic messages in *Xenopus laevis* embryos by modified oligonucleotides possessing terminal cationic linkages." *Nucleic Acids Res* 28(10): 2153-7.

deVries, A. A. F., M. C. Horzinek, et al. (1997). "The Genome Organization of the Nidovirales: Similarities and Differences between Arteri-, Toro-, and Coronaviruses*1." *Seminars in Virology* 8(1): 33-47.

Ding, D., S. M. Grayaznov, et al. (1996). "An oligodeoxyribonucleotide N3'→P5' phosphoramidate duplex forms an A-type helix in solution." *Nucleic Acids Res* 24(2): 354-60.

Felgner, P. L., T. R. Gadek, et al. (1987). "Lipofection: a highly efficient, lipid-mediated DNA-transfection procedure." *Proc Natl Acad Sci USA* 84(21): 7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin* 1] 0(14): 1684-6.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev* 8(2): 103-11.

Guan, Y., B. J. Zheng, et al. (2003). "Isolation and Characterization of Viruses Related to the SARS Coronavirus from Animals in Southern China." *Science:* 1087139.

Lai, M. M. and D. Cavanagh (1997). "The molecular biology of coronaviruses." *Adv Virus Res* 48: 1-100.

Lesnikowski, Z. J., M. Jaworska, et al. (1990). "Octa(thymidine methanephosphonates) of partially defined stereochemistry: synthesis and effect of chirality at phosphorus on binding to pentadecadeoxyriboadenylic acid." *Nucleic Acids Res* 18(8): 2109-15.

Marra, M. A., S. J. M. Jones, et al. (2003). "The Genome Sequence of the SARS-Associated Coronavirus." *Science* 300(5624): 1399-1404.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem* 12(1): 154-7.

Moulton, H. M. and J. D. Moulton (2003). "Peptide-assisted delivery of steric-blocking antisense oligomers." *Curr Opin Mol Ther* 5(2): 123-32.

Pasternak, A. O., W. J. Spaan, et al. (2004). "Regulation of relative abundance of arterivirus subgenomic mRNAs." *J Virol* 78(15): 8102-13.

Pasternak, A. O., E. van den Born, et al. (2001). "Sequence requirements for RNA strand transfer during nidovirus discontinuous subgenomic RNA synthesis." *Embo J* 20(24): 7220-8.

Pasternak, A. O., E. van den Born, et al. (2003). "The Stability of the Duplex between Sense and Antisense Transcription-Regulating Sequences Is a Crucial Factor in Arterivirus Subgenomic mRNA Synthesis." *J. Virol.* 77(2): 1175-1183.

Peiris, J. S., K. Y. Yuen, et al. (2003). "The severe acute respiratory syndrome." *N Engl J Med* 349(25): 2431-41.

Rota, P. A., M. S. Oberste, et al. (2003). "Characterization of a novel coronavirus associated with severe acute respiratory syndrome." *Science* 300(5624): 1394-9.

Sawicki, S. G. and D. L. Sawicki (1998). "A new model for coronavirus transcription." *Adv Exp Med Biol* 440: 215-9.

Siddell, S. G. (1995). *The Coronaviridae*. New York, Plenum Press.

Stein, D., E. Foster, et al. (1997). "A specificity comparison of four antisense types: morpholino, 2'-O-methyl RNA, DNA, and phosphorothioate DNA." *Antisense Nucleic Acid Drug Dev* 7(3): 151-7.

Strauss, J. H. and E. G. Strauss (2002). *Viruses and Human Disease*. San Diego, Academic Press.

Summerton, J. and D. Weller (1997). "Morpholino antisense oligomers: design, preparation, and properties." *Antisense Nucleic Acid Drug Dev* 7(3): 187-95.

Thiel, V., K. A. Ivanov, et al. (2003). "Mechanisms and enzymes involved in SARS coronavirus genome expression." *J Gen Virol* 84(Pt 9): 2305-15.

Toulme, J. J., R. L. Tinevez, et al. (1996). "Targeting RNA structures by antisense oligonucleotides." *Biochimie* 78(7): 663-73.

VAN DEN BORN, E., A. P. GULTYAEV, et al. (2004). "Secondary structure and function of the 5'-proximal region of the equine arteritis virus RNA genome." *RNA* 10(3): 424-437.

Zeng, L., E. K. Godeny, et al. (1995). "Analysis of simian hemorrhagic fever virus (SHFV) subgenomic RNAs, junction sequences, and 5' leader." *Virology* 207(2): 543-8.

Ziebuhr, J., E. J. Snijder, et al. (2000). "Virus-encoded proteinases and proteolytic processing in the Nidovirales." *J Gen Virol* 81(4): 853-879.

BACKGROUND OF THE INVENTION

The Nidovirales is a recently established order comprising the families Arteriviridae (genus Arterivirus) and Coronaviridae (genera Coronavirus and Torovirus). Despite noteworthy differences in genome size, complexity and virion architecture, coronaviruses, toroviruses and arteriviruses are remarkably similar in genome organization and replication strategy (de Vries, Horzinek et al 1997). The name Nidovirales is derived from the Latin nidus, to nest, and refers to the 3' coterminal nested set of subgenomic (sg) viral mRNAs produced during infection. Sequence comparisons of the replicase genes suggest that the Nidovirales have evolved from a common ancestor despite their substantial differences.

Coronaviruses cause about 30% of common colds in humans and, unlike rhinoviruses, cause both upper and lower respiratory infections, the latter being a more serious affliction. In addition, coronaviruses cause gastroenteritis and diarrhea in humans and many other serious diseases in non-human animals including mice, chickens, pigs and cats. Although no known human arteriviruses exist, arteriviruses cause a number of diseases in horses, pigs, mice and monkeys.

The most well-known human coronavirus has only recently appeared and is responsible for severe acute respiratory syndrome (SARS), a life threatening form of pneumonia (Peiris, Yuen et al 2003). SARS is caused by a previously unknown coronavirus named SARS coronavirus (SARS-CoV). First appearing in November 2002, an epidemic emerged that spread from its zoonotic origin in Guangdong Province, China, to 26 countries on five continents. By August 2003, a cumulative total of 8422 cases and 774 deaths had been recorded by the World Health Organization. The rapid transmission by aerosols and the fecal-oral route and the high mortality rate (11%) make SARS a potential global threat for which no efficacious therapy is available.

No vaccines for coronaviruses or arteriviruses (Nidoviruses) are available and no effective antiviral therapies are available to treat an infection. As with many other human viral pathogens, available treatment involves supportive measures such as anti-pyretics to keep fever down, fluids, antibiotics for secondary bacterial infections and respiratory support as necessary.

In view of the severity of the diseases caused by Nidoviruses and the lack of effective prevention or therapies, it is therefore an object of the present invention to provide therapeutic compounds and methods for treating a host infected with a coronavirus, torovirus or arterivirus.

SUMMARY OF THE INVENTION

In one aspect, the invention includes an oligonucleotide compound for use in inhibiting replication of a nidovirus in human cells. The compound is characterized by: (i) a nuclease-resistant backbone, (ii) capable of uptake by virus-infected human cells, (iii) containing between 8-25 nucleotide bases, and (iv) having a sequence that is complementary to at least 8 bases contained in one of:

(1) a sequence in a 5' leader sequence of the nidovirus' positive-strand genomic RNA from the group SEQ ID NOS: 1-9, each sequence of which includes an internal leader transcriptional regulatory sequence; and, (2) a sequence in a negative-strand 3' subgenomic region of the virus from the group exemplified by SEQ ID NOS: 10-19, each sequence of which includes an internal body transcriptional regulatory sequence that is substantially complementary to the corresponding leader transcriptional regulatory sequence.

The compound is capable of forming with the nidovirus (1) positive-strand genomic RNA or (2) the negative-strand 3' subgenomic region, a heteroduplex structure characterized by (1) a Tm of dissociation of at least 45° C., and (2) a disrupted base pairing between the transcriptional regulatory sequences in the 5' leader region of the positive-strand viral genome and negative-strand 3' subgenomic region.

The compound may be composed of morpholino subunits and phosphorus-containing intersubunit linkages joining a morpholino nitrogen of one subunit to a 5' exocyclic carbon of an adjacent subunit. Exemplary intersubunit linkages are phosphorodiamidate linkages in accordance with the structure:

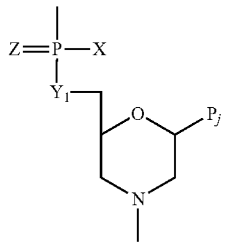

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino.

In one general embodiment, the compound has a sequence complementary to at least 8 bases contained in the 5' leader sequence of the nidovirus' positive-strand genomic RNA from the group SEQ ID NOS: 1-9. The compound sequence is preferably complementary to at least a portion of the transcriptional regulatory sequence contained within one of the sequences SEQ ID NOS: 1-9. Exemplary compound sequences in this embodiment include SEQ ID NOS: 20-35.

The compound may be composed of morpholino subunits linked with the uncharged linkages described above interspersed with linkages that are positively charged at physiological pH. The total number of positively charged linkages is between 2 and no more than half of the total number of linkages. The positively charged linkages may have the structure above, where X is 1-piperazine.

For use in inhibiting replication of human SARS virus, the compound may contain one of sequences SEQ ID NOS: 26 and 27. For use in inhibiting replication of human coronavius-229E or human coronavirus-OC43, the compound may contain one of the sequences SEQ ID NOS: 22 or 23, for the coronavirus-229E, and the sequence SEQ ID NOS: 24 or 25, for the coronavirus-OC43. For use in inhibiting replication of feline coronavirus, the compound may contain SEQ ID NOS: 20 or 21.

In another general embodiment, the compound has a sequence complementary to at least 8 bases contained in the negative-strand 3' subgenomic region of the virus exemplified by the group SEQ ID NOS: 10-19. The compound preferably has a sequence complementary to at least a portion of the minus-strand body transcriptional regulatory sequence contained within one of the sequences SEQ ID NOS: 10-19. Exemplary compound sequences in this embodiment contain a sequence from the group SEQ ID NOS: 36-45.

For use in inhibiting replication of human SARS virus, the compound may contain one of the sequences SEQ ID NOS: 36-43. For use in inhibiting replication of simian hemorrhagic fever virus, the compound may contain the SEQ ID NOS: 44 and 45.

In the method of the invention for inhibiting nidovirus replication in virus-infected cells, the cells are exposed to the oligonucleotide compound, in an amount sufficient to inhibit nidovirus replication in the virus-infected cells. The inhibition is due to base-pair binding of the compound to (1) a sequence in a 5' leader sequence of the nidovirus' positive-strand genomic RNA that includes an internal leader transcriptional regulatory sequence, or (2) a sequence in a negative-strand 3' subgenomic region of the virus that includes an internal body transcriptional regulatory sequence that is substantially complementary to the corresponding transcriptional regulatory sequence contained the 5' leader sequence. This base-pair binding forms a viral-RNA/compound heteroduplex characterized by (1) a $T_m$ of dissociation of at least 45° C., and (2) a disrupted base pairing between the transcriptional regulatory sequences in the 5' leader region of the positive-strand viral genome and negative-strand 3' subgenomic region. Various embodiments of the compound, noted above, are incorporated into the method.

For use in treating a nidovirus infection in a human or veterinary-animal subject, the compound may be administered orally to the subject, to contact the compound with the virus-infected cells. The method may further include monitoring a subject body fluid for the appearance of a heteroduplex composed of the oligonucleotide compound and a complementary portion of the viral genome in positive- or negative-strand form.

These and other objects and features of the invention will become more fully apparent when the following detailed description of the invention is read in conjunction with the accompanying drawings.

BRIEF DESCRIPTION OF THE DRAWINGS

FIG. 2B indicates the point at which antisense oligomers targeted to the 5' positive-strand leader transcriptional regulatory sequence interfere with this process. Also shown in FIG. 2B is an antisense oligomer targeted to the 3' minus-strand body transcriptional regulatory sequence.

DETAILED DESCRIPTION OF THE INVENTION

I. Definitions

The terms below, as used herein, have the following meanings, unless indicated otherwise:

The terms "oligonucleotide analog" refers to oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 50-100%, are uncharged at physiological pH, and contain a single phosphorous atom. The analog contains between 8 and 40 subunits, typically about 8-25 subunits, and preferably about 12 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide analog" is an oligonucleotide analog composed of morpholino subunit structures of the form shown in FIGS. 3A-3D, where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

Figure 3A:
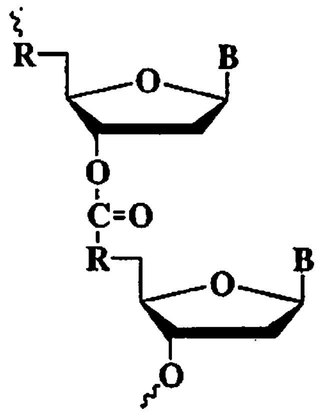
FIG. 3A-3G show the backbone structures of various oligonucleotide analogs with uncharged backbones and FIG. 3H shows a preferred cationic linkage.
Figure 3B:
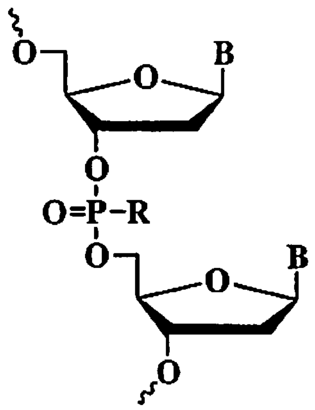
Figure 3C:
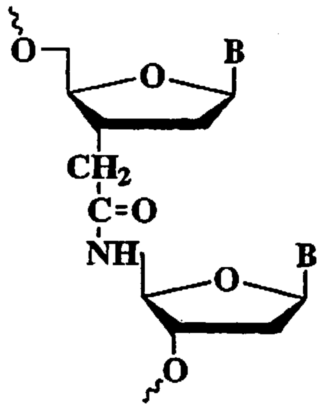
Figure 3D:
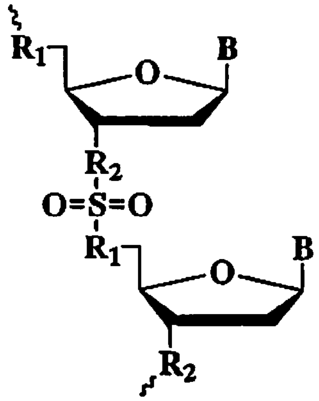
Figure 3E:
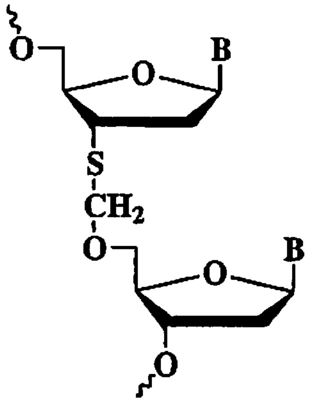
Figure 3F:
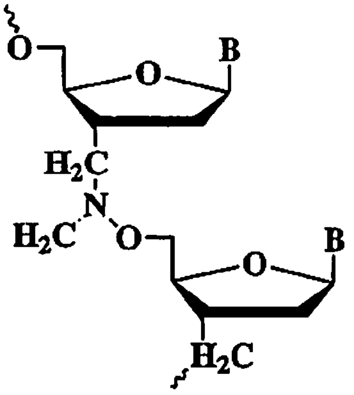

The subunit and linkage shown in FIG. 3B are used for six-atom repeating-unit backbones, as shown in FIG. 3B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_1$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

Figure 2A:
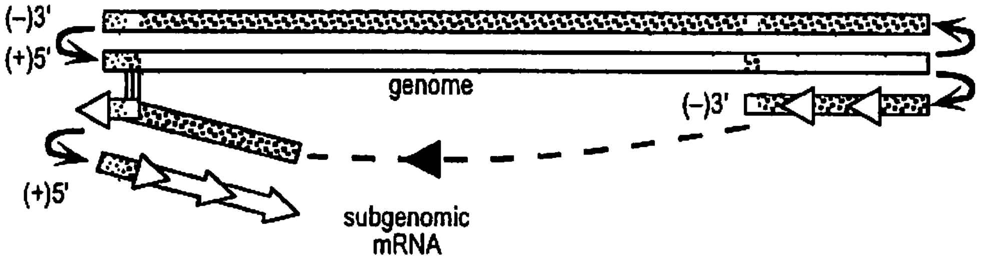
FIG. 2A-2B is a schematic representation of Nidovirus RNA replication and the process of discontinuous transcription that results in a nested set of 3'co-terminal subgenomic mRNAs with a common 5' leader sequence.
Figure 2B:
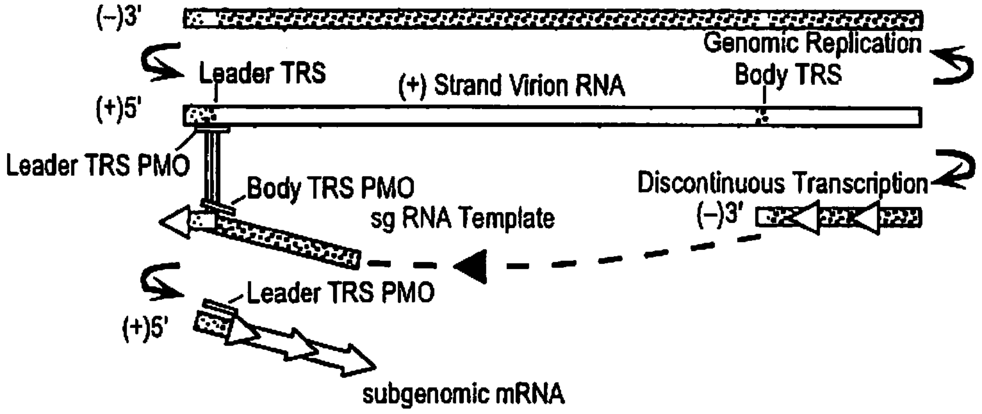
Figure 3G:
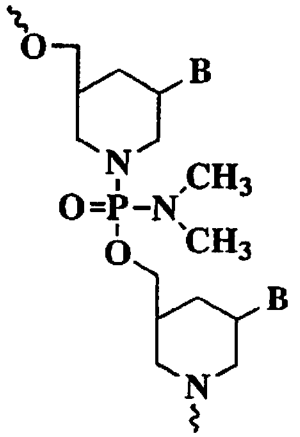
Figure 3H:
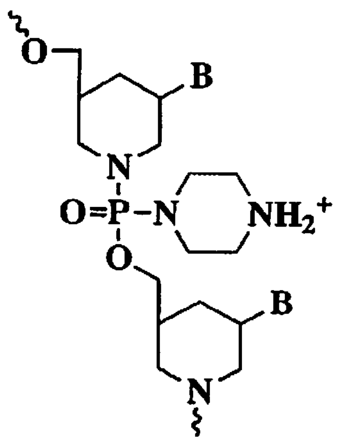

A preferred morpholino oligomer is a phosphorodiamidate-linked morpholino oligomer, referred to herein as a PMO. Such oligomers are composed of morpholino subunit structures such as shown in FIG. 2B, where X═NH2, NHR, or NR2 (where R is lower alkyl, preferably methyl), Y═O, and Z═O, and Pi and Pj are purine or pyrimidine base-pairing moieties effective to bind, by base-specific hydrogen bonding, to a base in a polynucleotide, as seen in FIG. 3G. Also preferred are morpholino oligomers where the phosphordiamidate linkages are uncharged linkages as shown in FIG. 3G interspersed with cationic linkages as shown in FIG. 3H where, in FIG. 2B, X=1-piperazino. In another FIG. 2B embodiment, X=lower alkoxy, such as methoxy or ethoxy, Y═NH or NR, where R is lower alkyl, and Z═O.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "target", relative to the viral genomic RNA, refers to a viral genomic RNA, and may include either the positive strand RNA which is the replicative strand of the virus, or the negative or antisense strand which is formed in producing multiple new copies of the positive-strand RNA.

The term "target sequence" refers to a portion of the target RNA against which the oligonucleotide analog is directed, that is, the sequence to which the oligonucleotide analog will hybridize. The target sequence includes at least a portion of one of the sequences identified as SEQ ID NOS: 1-9, representing the genome's leader transcriptional regulatory sequence in a member of the Nidovirales, as discussed further below. Another target sequence includes at least a portion of the 3' minus-strand body transcriptional regulatory sequence exemplified by SEQ ID NOS: 10-19.

The term "targeting sequence" is the sequence in the oligonucleotide analog that is complementary or substantially complementary to the target sequence in the RNA genome. The entire sequence, or only a portion of, the analog may be complementary to the target sequence, or only a portion of the total analog sequence. For example, in an analog having 20 bases, only 8-12 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence. As will be seen, the target and targeting sequences are selected such that binding of the analog to part of the viral genome acts to disrupt or prevent formation of subgenomic RNA formed by the interaction between leader and body transcriptional regulatory sequences.

Target and targeting sequences are described as "complementary" to one another when hybridization occurs in an antiparallel configuration. A double-stranded polynucleotide can be "complementary" to another polynucleotide. A targeting sequence may have "near" or "substantial" complementarity to the target sequence and still function for the purpose of the present invention. Preferably, the oligonucleotide analogs employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonculeotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAseH, which are capable of cutting double-stranded RNA/RNA or RNA/DNA complexes.

A "base-specific intracellular binding event involving a target RNA" refers to the specific binding of an oligonucleotide analog to a target RNA sequence inside a cell. The base specificity of such binding is sequence specific. For example, a single-stranded polynucleotide can specifically bind to a single-stranded polynucleotide that is complementary in sequence.

An "effective amount" of an antisense oligomer, targeted against an infecting ssRNA virus, is an amount effective to reduce the rate of replication of the infecting virus, and/or viral load, and/or symptoms associated with the viral infection.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide analog preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. The analog may be conjugated, e.g., at its 5' or 3' end, to an arginine rich peptide, e.g., the HIV TAT protein, or polyarginine, to facilitate transport into the target host cell.

The term "coronavirus" is used herein to include all members of the Coronaviridae family including viruses of the Coronavirus and Torovirus genera. The term "arterivirus" includes members of the Arteriviridae family which includes the Arterivirus genera. The term "Nidovirus" refers to viruses of the Nidovirales order which includes the families Coronaviridae and Arteriviridae. Representative Nidoviruses are listed in Table 1. below.

TABLE 1

Representative Nidoviruses

| Virus Name | Abbreviation |
|---|---|
| Canine coronavirus | CCoV |
| Feline coronavirus | FCoV |
| Human coronavirus 229E | HCoV-229E |
| Porcine epidemic diarrhea virus | PEDV |
| Transmissible gastroenteritis virus | TGEV |
| Porcine Respiratory Coronavirus | PRCV |
| Bovine coronavirus | BCoV |
| Human coronavirus OC43 | HCoV-OC43 |
| Murine hepatitis virus | MHV |
| Rat coronavirus | RCV |
| Infectious bronchitis virus | IBV |
| Turkey coronavirus | TCoV |
| Rabbit coronavirus | RbCoV |
| SARS coronavirus | SARS-CoV |
| Human torovirus | HuTV |
| Equine arteritis virus | EAV |
| Porcine reproductive and respiratory syndrome virus | PRRSV |
| Porcine hemagglutinating encephalomyelitis virus | PHEV |
| Simian hemorrhagic fever virus | SHFV |

II. Target Coronaviruses and Arteriviruses

The present invention is based on the discovery that effective inhibition of coronavirus replication can be achieved by exposing coronavirus-infected cells to oligomeric analogs (i) targeted to the transcriptional regulatory sequence (TRS) region of coronavirus RNA and (ii) having physical and pharmacokinetic features which allow effective interaction between the analog and the viral RNA within host cells. In one aspect, the analogs can be used in treating a mammalian subject infected with the virus.

The invention targets members of the Coronaviridae and Arteriviridae families of the Nidovirales order including, but not limited to, the viruses described below. Various physical, morphological, and biological characteristics of the genes, and members therein, can be found, for example, in (Strauss and Strauss 2002), and in one or more of the references cited herein. Some of the key biological, pathological and epidemiological characteristics of representative nidoviruses are summarized below. Recent reviews on coronaviruses are available (e.g. see (Siddell 1995; Lai and Cavanagh 1997) and are incorporated herein in their entirety.

A. Human Coronaviruses

Coronaviruses are known to cause approximately 30% of common colds in humans. The most studied of these are human coronaviruses HCoV-229E and HCoV-OC43. These viruses are spread by the respiratory route and, unlike rhinoviruses, cause both upper and lower respiratory tract infections. Lower respiratory tract infections are considered more serious clinically. In addition to these viruses, human torovirus (HuTV) causes gastroenteritis and diarrhea in infected individuals.

The SARS-CoV causes a life-threatening form of pneumonia called severe acute respiratory syndrome (SARS). From its likely zoonotic origin in Guangdong Province, China in November 2002, the SARS-CoV spread rapidly to 29 countries, infected over 8400 individuals and caused more than 750 deaths (Peiris, Yuen et al 2003). The rapid transmission by aerosols and probably the fecal-oral route coupled with the high mortality rate make SARS a global threat for which no efficacious therapy is available. There is evidence that natural infection with SARS-CoV occurs in a number of animal species indigenous to China and parts of southeast Asia (Guan, Zheng et al 2003). Genome sequences of SARS-CoV isolates obtained from a number of index patients have been published recently (Marra, Jones et al 2003; Rota, Oberste et al 2003). A virus closely related genetically to SARS-CoV was isolated from several animals obtained from a market in Quangdong Province. Sequencing of the viruses obtained from these animals demonstrated that the most significant difference between them and SARS-CoV was an additional 29 base-pair sequence in the animal viruses. The role of animals in the transmission of SARS-CoV to humans and whether an animal reservoir for the virus exists is the subject of active, ongoing research.

B. Animal Coronaviruses and Arteriviruses

Coronaviruses and Arteriviruses for many other animals are known, including mice chickens, pigs, and cats. Associated diseases include respiratory disease, gastroenteritis, hepatitis, and a syndrome similar to multiple sclerosis of humans, among many other illnesses. Mouse hepatitis virus (MHV) has been particularly well studied and, along with the Arterivirus equine arteritis virus (EAV) has been the prototypic molecular model system for the Nidovirales order.

One animal coronavirus that causes significant animal mortality is feline infectious peritonitis virus, the leading cause of death in young domestic cats. The feline coronaviruses (FCOV) generally do not cause infections with high morbidity but in a small percentage of cases, the virus mutates to become more virulent. This virus, feline infectious peritonitis virus (FIPV), causes severe disease in young cats. This disease is in large part immunopathological and understanding it is a major goal of coronavirus research. The infection causes lesions in many organs, most prominently in the liver and spleen. The disease is further characterized by disseminated inflammation and serositis in the abdominal and thoracic cavities. In addition to this "wet" or effusive form, a "dry" or noneffusive form of feline infectious peritonitis (FIP) also occurs. Both forms are different manifestations of the same infection. Despite many studies, the pathogenesis of FIP is still not well understood.

Another serious non-human Nidovirus is porcine reproductive and respiratory syndrome virus (PRRSV), an arterivirus similar to EAV and SHFV. The disease caused by PRRSV causes reproductive failure in sows, pre-weaning mortality and respiratory tract illness that can have severe consequences, especially in piglets (Allende, Lewis et al. 1999). This virus causes significant losses in the pig industry with associated economic ramifications.

III. Coronavirus and Arterivirus Replication and Gene Expression

Figure 1:
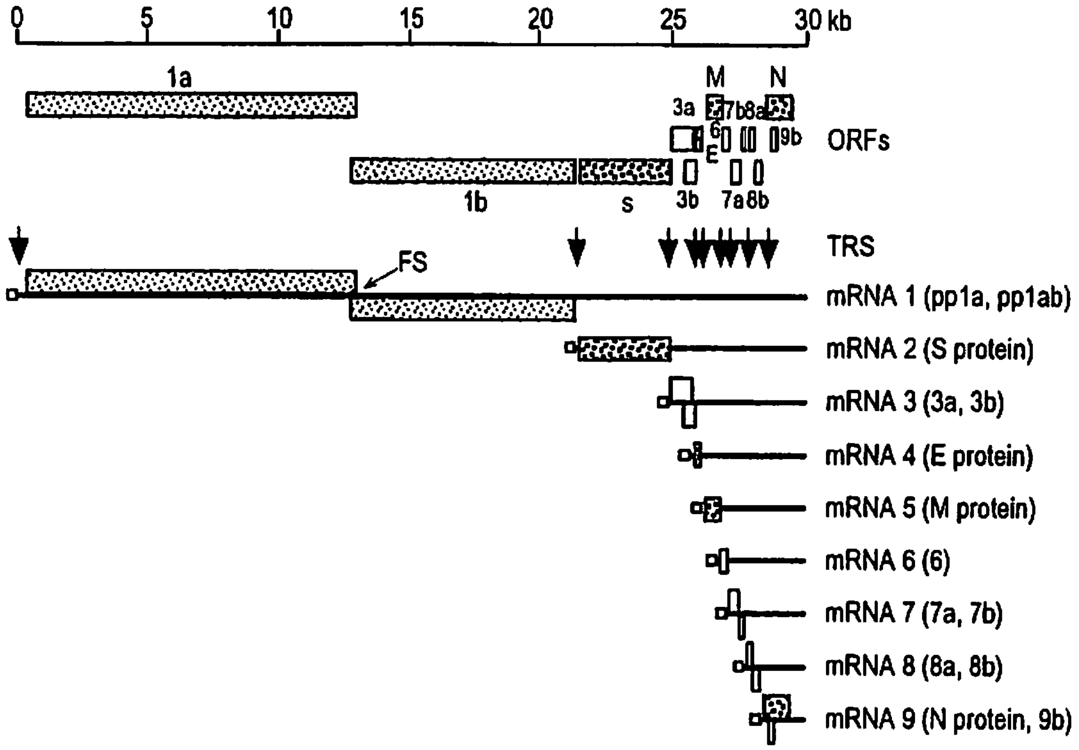
FIG. 1 shows a genetic map and predicted viral proteins of the SARS coronavirus which is representative of the genome organization of all Nidoviruses. Also shown are the eight subgenomic mRNAs (mRNA 2-8) that are produced. The small black boxes at the 5' end of the genomic and subgenomic RNAs represent the common 72 nucleotide leader RNA sequence derived from the 5' terminal 72 nucleotides of the genomic RNA during discontinuous transcription.

Coronaviruses encode an RNA genome that is capped, polyadenylated, nonsegmented, infectious, positive-strand, approximately 30 kb and considered the largest of all known viral RNA genomes. Arteriviruses have a 13 kb genome that is very similar in organization and expression strategy to that of coronaviruses. The 5' two-thirds of the coronavirus genome is occupied by the open reading frame (ORF) 1a and ORF 1b which encode the replicase proteins of the virus. These genes are translated from infecting genomic RNA into two polyprotein precursors which produce the viral replication and transcription functions. Downstream of ORF 1b a number of genes occur that encode structural and several nonstructural, accessory proteins. These genes are expressed through a 3'-coterminal nested set of subgenomic mRNAs (sg mRNAs) that are synthesized by a process of discontinuous transcription. The sg mRNAs represent variable lengths of the 3' end of the viral genome, each one provided at its 5' end with a sequence identical to the genomic 5' "leader" sequence. The mRNAs are each functionally monocistronic (i.e. the proteins are translated only from the 5'-most ORF). A schematic that illustrates the gene organization and sg mRNAs of SARS-CoV is shown in FIG. 1 (Thiel, Ivanov et al 2003).

The control of gene expression by discontinuous transcription is novel and unique to a small number of single stranded RNA viruses, most notably the Nidovirales order (de Vries, Horzinek et al. 1997). FIG. 2A provides a schematic of the replication and transcriptional mechanism employed by members of the Nidovirales (Pasternak, van den Born et al. 2001). As with most single stranded, positive-sense RNA viruses, the infecting RNA is translated to yield the viral-encoded RNA polymerase or replicase. The RNA polymerase then produces either full length negative-sense RNA, used as a template for additional full-length, positive-sense genomic RNA synthesis, or a series of negative-sense subgenomic (sg) RNAs which serve as templates for synthesis of the complementary, positive-sense sg mRNAs. This process is termed discontinuous transcription (Sawicki and Sawicki 1998). Negative-sense sg RNAs are produced by a mechanism in which the viral RNA polymerase copies the 3' end of the genomic RNA template and completes synthesis by "jumping" to finish copying the immediate 5' end. The negative-sense RNAs are then used to synthesize individual sg mRNAs. Each sg mRNA contains the same 5' end sequence approximately 70 nucleotides long (approximately 200 nucleotides in the Arteriviridae) called the leader sequence. Coronavirus gene expression is regulated at the level of transcription primarily through the mechanism of discontinuous transcription of the negative-sense templates.

The fusion of the noncontiguous sequences during discontinuous transcription is believed to be achieved through the involvement of transcriptional regulatory sequences (TRSs). The TRS sequences are short, 6-12 nucleotide regions that are found at the 3' end of the leader sequence (leader TRS), and upstream of the genes in the 3'-proximal part of the genome (body TRSs). The TRSs are homologous and are believed to function by a mechanism where the minus-strand body TRS "jumps" to the complementary leader TRS on the positive-sense strand where it "lands" (i.e., the two TRSs hybridize) allowing completion of the synthesis of the negative-sense leader sequence (i.e., see FIG. 2A) (Pasternak, van den Born et al. 2001).

IV. Antisense Targeting of Nidovirus Transcriptional Regulatory Sequences

The preferred target sequences are those nucleotide sequences adjacent and including at least a portion, e.g., at least 2-8 bases, of the leader TRS of the positive—RNA or the minus-strand body TRS of Nidovirus RNA. As discussed above, the TRSs appear to play a critical role in viral transcription by bringing into close proximity the minus-strand body TRS and positive-strand leader TRS in order to complete synthesis of the negative-sense sg RNA templates. FIG. 2B provides a schematic representation of how and where antisense oligomers interfere with the process of discontinuous transcription at these two target sites.

A variety of Nidovirus genome sequences are available from well known sources, such as the NCBI Genbank databases. Alternatively, a person skilled in the art can find sequences for many of the subject viruses in the open literature, e.g., by searching for references that disclose sequence information on designated viruses. Once a complete or partial viral sequence is obtained, the leader TRS sequence of the virus is identified.

GenBank references for exemplary viral nucleic acid sequences containing the leader TRS or body TRS in the corresponding viral genomes are listed in Table 2 below. It will be appreciated that these sequences are only illustrative of other Nidovirus sequences, as may be available from available gene-sequence databases or literature or patent resources. The sequences below, identified as SEQ ID NOS: 1-19, are also listed in Table 4 at the end of the specification. The bold nucleotides in Table 2 identify the core leader TRS or the body minus-strand TRS.

TABLE 2

Exemplary TRS Target Sequences

| Virus | GenBank Acc. No. | Leader TRS Ncts. | SEQ ID NO. | Target Sequence (5' to 3') |
|---|---|---|---|---|
| FCoV | AY204705 | 109-135 | 1 | cggacaccaacucga**acuaaac**gaaau |
| TGEV | AJ271965 | 78-104 | 2 | cggacaccaacucga**acuaaac**gaaau |
| HCoV-229E | AF304460 | 55-78 | 3 | cuacuuuucuca**acuaaac**gaaau |
| HCoV-OC43 | AY391777 | 51-74 | 4 | gaucuuuuguaa**ucuaaac**uuua |
| SARS-CoV | AY274119 | 53-76 | 5 | gaucuguucucuaa**acgaac**uuua |
| MHV | AF029248 | 50-75 | 6 | guaguuuaaaucu**aaucuaaac**uuua |
| SHFV | AF180391 | 188-215 | 7 | gauuugcagacccucc**uuaacc**auguuc |
| PRRSV | AF046869 | 168-194 | 8 | cggucucuccaccccuuu**aacc**auguc |
| EAV | X53459 | 189-228 | 9 | caucgucgucgaucucua**ucaacu**acccuugcgacuaugg |

| Virus | GenBank Acc. No. | Body Minus-Strand TRS Ncts. | SEQ ID NO. | Target Sequence (5' to 3'-minus strand) |
|---|---|---|---|---|
| SARS-CoV | AY291315 | 21482-21502 | 10 | aaaauaaacau**guucgu**uuag |
| SARS-CoV | AY291315 | 25257-25277 | 11 | acaaauccauaa**guucgu**uua |
| SARS-CoV | AY291315 | 26109-26129 | 12 | cgaaugaguacauaa**guucgu** |
| SARS-CoV | AY291315 | 26343-26363 | 13 | auaauaguua**guucgu**uuaga |
| SARS-CoV | AY291315 | 26913-26933 | 14 | uuguaauaagaaagc**guucgu** |
| SARS-CoV | AY291315 | 27265-27285 | 15 | gaauaauuuucau**guucguuu** |
| SARS-CoV | AY291315 | 27768-27788 | 16 | gaaguuucau**guucgu**uuaga |
| SARS-CoV | AY291315 | 28103-28123 | 17 | acauuuuaauuu**guucgu**uua |
| SHFV | AF180391 | 14699-14719 | 18 | ucagcacgucgucgu**gguuga** |
| SHFV | AF180391 | 15280-15300 | 19 | agccauacuuccuca**gguuaa** |

TABLE 2-continued

The degree of complementarity between the target and targeting sequence is sufficient to form a stable duplex. The region of complementarity of the antisense oligomers with the target RNA sequence may be as short as 8-11 bases, but is preferably 12-15 bases or more, e.g. 12-20 bases, or 12-25 bases. An antisense oligomer of about 15 bases is generally long enough to have a unique complementary sequence in the viral genome. In addition, a minimum length of complementary bases may be required to achieve the requisite binding $T_m$, as discussed below.

Oligomers as long as 40 bases may be suitable, where at least a minimum number of bases, e.g., 12 bases, are complementary to the target sequence. In general, however, facilitated or active uptake in cells is optimized at oligomer lengths less than about 30, preferably less than 25. For PMO oligomers, described further below, an optimum balance of binding stability and uptake generally occurs at lengths of 15-22 bases.

The oligomer may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g. discontinous transcription, is modulated.

The stability of the duplex formed between the oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108. Each antisense oligomer should have a binding $T_m$, with respect to a complementary-sequence RNA, of greater than body temperature and preferably greater than 45° C. $T_m$'s in the range 60-80° C. or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 15 bases or less are generally preferred over those requiring 20+ bases for high $T_m$ values.

The antisense activity of the oligomer may be enhanced by using a mixture of uncharged and cationic phosphorodiamidate linkages as shown in FIGS. 2G and 2H. The total number of cationic linkages in the oligomer can vary from 1 to 10, and be interspersed throughout the oligomer. Preferably the number of charged linkages is at least 2 and no more than half the total backbone linkages, e.g., between 2-8 positively charged linkages, and preferably each charged linkages is separated along the backbone by at least one, preferably at least two uncharged linkages. The antisense activity of various oligomers can be measured in vitro by fusing the oligomer target region to the 5' end a reporter gene (e.g. firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

Table 3 below lists exemplary targeting sequences directed against the leader TRS or minus-strand body TRS for selected Nidoviruses. These sequences, identified by SEQ ID NOS: 20-46, are complementary and antiparallel to the target sequences identified as SEQ ID NOS: 1-19 above. As noted above, the actual targeting sequence in the oligonucleotide analog may be complementary to only a portion of the corresponding target sequence in Table 2.

More generally, the invention contemplates, as exemplary targeting sequences, a sequence of at least 8 bases complementary to a region of the virus' positive-strand RNA genome that includes at least a portion of the genome's positive-strand leader TRS. In addition, exemplary targeting sequences are sequences of at least 8 bases complementary to a region of the virus' negative strand that includes at least a portion of the genome's negative-strand body TRS. The targeting sequence contains a sufficient number of bases in either of the TRSs to disrupt base pairing between the virus leader and body TRS sequences. The number of targeting sequences needed to disrupt this structure is preferably at least 2-4 bases complementary to the core leader or body TRS (shown in bold in Table 2), plus bases complementary to adjacent target-sequence bases.

The exemplary targeting sequences in Table 3 below and target sequences in Table 2 for minus-strand body TRSs correspond to individual subgenomic messenger RNAs (sg mRNAs). For SARS-CoV, sg mRNA targets and targeting sequences for mRNA2 through mRNA9 correspond to SEQ ID NOS: 10-17 and SEQ ID NOS: 36-43, respectively (Thiel, Ivanov et al. 2003). For SHFV, sg mRNAs targets and targeting sequences for mRNA 6 and 7 correspond to SEQ ID NOS: 18 and 19 and SEQ ID NOS: 44 and 45, respectively (Zeng, Godeny et al 1995).

TABLE 3

Exemplary Targeting Sequences Against the Leader TRS of Nidoviruses

| Virus(es) | GenBank Acc No. | Leader TRS Targeting Sequences (5' to 3') | SEQ ID NO. |
|---|---|---|---|
| FCoV | AY204705 | 5'-ATTTCGTTTAGTTCGA GTTGG-3' | 20 |
| TGEV | AJ271965 | 5'-GTTTAGTTCGAGTTGG TGTCCG-3' | 21 |
| CaCoV PRCV | N/A X52668 | | |
| HCOV | AF304460 | 5'-ATTTCGTTTAGTTGAG AAAAG-3' | 22 |

TABLE 3-continued

Exemplary Targeting Sequences Against the Leader TRS of Nidoviruses

| Virus(es) | GenBank Acc No. | Leader TRS Targeting Sequences (5' to 3') | SEQ ID NO. |
|---|---|---|---|
| 229E | | 5'-GTTTAGTTGAGAAAAG TAG-3' | 23 |
| HCoV | AY391777 | 5'-TAAAGTTTAGATTACA AAAAG-3' | 24 |
| OC43 | AF220295 | 5'-GTTTAGATTACAAAAA GATC-3' | 25 |
| BCoV PHEV | AF523845 | | |
| SARS | AY274119 | 5'-TAAAGTTCGTTTAGAG AACAG-3' | 26 |
| CoV | | 5'-GTTCGTTTAGAGAACA GATC-3' | 27 |
| MHV | AF029248 | 5'-TAAAGTTTAGATTAGA TTTAAAC-3' | 28 |
| | | 5'-GTTTAGATTAGATTTA AACTAC-3' | 29 |
| SHFV | AFI 80391 | 5'-GAACATGGTTAAGGAG GGTCTG-3' | 30 |
| | | 5'-GGTTAAGGAGGGTCTG CAAATC-3' | 31 |
| PRRSV | AF046869 | 5'-GACATGGTTAAAGGGG TGGAG-3' | 32 |
| | | 5'-GGTTAAGGGTTAAAGG GGTGGAGAGACCG-3' | 33 |
| EAV | X53459 | 5'-GGGTAGTTGATAGAGA TCGACG-3' | 34 |
| | | 5'-AGTTGATAGAGATCGA CGACGATG-3' | 35 |
| | | 5'-CCATAGTCGCAAGGGT AGTTGA-3' | 46 |
| SARS-cov | AY274119 | 5'-CTAAACGAACATGTTT ATTTT-3' | 36 |
| SARS-cov | AY274119 | 5'-TAAACGAACTTATGGA TTTGT-3' | 37 |
| SARS-cov | AY274119 | 5'-ACGAACTTATGTACTC ATTCG-3' | 38 |
| SARS-cov | AY274119 | 5'-TCTAAACGAACTAACT ATTAT-3' | 39 |
| SARS-cov | AY274119 | 5'-ACGAACGCTTTCTTAT TACAA-3' | 40 |
| SARS-cov | AY274119 | 5'-AAACGAACATGAAAAT TATTC-3' | 41 |
| SARS-cov | AY274119 | 5'-TCTAAACGAACATGAA ACTTC-3' | 42 |
| SARS-cov | AY274119 | 5'-TAAACGAACAAATTAA AATGT-3' | 43 |
| SHFV | AFI80391 | 5'-TCAACCACGACGACGT GCTGA-3' | 44 |
| SHFV | AFI80391 | 5'-TTAACCTGAGGAAGTA TGGCT-3' | 45 |

Note that the target sequence in Table 3 is indicated as containing uracil (U) bases characteristic of RNA, and the targeting sequences in Table 3, as containing thymine bases characteristic of DNA. It will be understood that the targeting sequence bases may be normal DNA bases or analogs thereof, e.g., uracil, that are capable of Watson-Crick base pairing to target-sequence RNA bases. Also note that where more than one virus is listed for any given targeting sequence, there is sufficient sequence homology for the targeting sequences to effectively hybridize to those viral targets.

IV. Antisense Oligomers

A. Properties

As detailed above, the antisense oligomer has a base sequence directed to a targeted portion of the viral genome, preferably the leader TRS and adjacent nucleotides. In addition, the oligomer is able to effectively target infecting viruses, when administered to an infected host cell, e.g. in an infected animal subject. This requirement is met when the oligomer compound (a) has the ability to be actively taken up by mammalian cells, and (b) once taken up, form a duplex with the target ssRNA with a $T_m$ greater than about 50° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

A1. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, and a comparable number of cationic linkages, such as N,N-diethylenediamine phosphoramidates (Dagle, Littig et al 2000). The net charge is preferably neutral or at most 1-2 net charges per oligomer.

In addition to being substantially or fully uncharged, the antisense agent is preferably a substrate for a membrane transporter system (i.e. a membrane protein or proteins) capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer, e.g., a phosphorothioate oligomer, on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin® (Felgner, Gadek et al 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked to the 5' or 3' end of the antisense oligomer. The peptide is typically 8-16 amino acids and consists of a mixture of arginine, and other amino acids including phenyalanine and cysteine. Exposure of cells to the peptide conjugated oligomer results in enhanced intracellular uptake and delivery to the RNA target.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

A2. Substantial Resistance to RNaseH

Two general mechanisms have been proposed to account for inhibition of expression by antisense oligonucleotides (Agrawal, Mayrand et al. 1990; Bonham, Brown et al 1995; Boudvillain, Guerin et al 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing, translation, or replication. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3'→P5' phosphoramidates (Ding, Grayaznov et al. 1996; Gee, Robbins et al 1998).

A test oligomer can be assayed for its RNaseH resistance by forming an RNA:oligomer duplex with the test compound, then incubating the duplex with RNaseH under a standard assay conditions, as described in Stein et al (Stein, Foster et al 1997). After exposure to RNaseH, the presence or absence of intact duplex can be monitored by gel electrophoresis or mass spectrometry.

A3. In Vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent application Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into an animal, e.g., a mammalian subject. The antisense oligomer may be directed against any intracellular RNA, including a host RNA or the RNA of an infecting virus. Several hours (typicaly 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as the region encompassing the Nidovirus leader TRS), the method can be used to detect the presence of a given ssRNA virus. The method can also be use to monitor the reduction in the amount of virus during a treatment method.

B. Exemplary Oligomer Backbones

Examples of nonionic linkages that may be used in oligonucleotide analogs are shown in FIGS. 3A-3G. In these figures, B represents a purine or pyrimidine base-pairing moiety effective to bind, by base-specific hydrogen bonding, to a base in a polynucleotide, preferably selected from adenine, cytosine, guanine, uracil and inosine. Suitable backbone structures include carbonate (3A, R═O) and carbamate (3A, R═$NH_2$) linkages (Mertes and Coats 1969; Gait, Jones et al. 1974); alkyl phosphonate and phosphotriester linkages (3B, R=alkyl or —O-alkyl) (Lesnikowski, Jaworska et al. 1990); amide linkages (3C) (Blommers, Pieles et al. 1994); sulfone and sulfonamide linkages (3D, $R_1$, $R_2$═$CH_2$) (Roughten, 1995; McElroy, 1994); and a thioformacetyl linkage (3E) (Matteucci, 1990; Cross, 1997). The latter is reported to have enhanced duplex and triplex stability with respect to phosphorothioate antisense compounds (Cross, 1997). Also reported are the 3'-methylene-N-methylhydroxyamino compounds of structure 3F (Mohan, 1995). Also shown is a cationic linkage in FIG. 3H wherein the nitrogen pendant to the phosphate atom in the linkage of FIG. 3G is replaced with a 1-piperazino structure. The method for synthesizing the 1-piperazino group linkages is described below with respect to FIG. 10.

Peptide nucleic acids (PNAs) (FIG. 3G) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm et al., 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 4A-4D. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: the ability to be linked in a oligomeric form by stable, uncharged backbone linkages; the ability to support a nucleotide base (e.g. adenine, cytosine, guanine or uracil) such that the polymer formed can hybridize with a complementary-base target nucleic acid, including target RNA, with high $T_m$, even with oligomers as short as 10-14 bases; the ability of the oligomer to be actively transported into mammalian cells; and the ability of the oligomer:RNA heteroduplex to resist RNAse degradation.

Figure 4A:
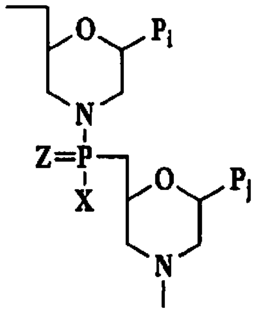
FIGS. 4A-4D show the repeating subunit segment of exemplary morpholino oligonucleotides, designated 3A-3D.
Figure 4B:
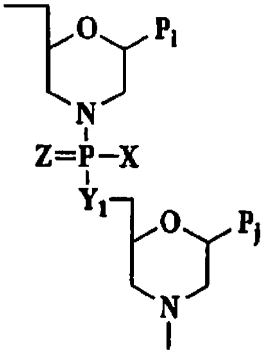

Exemplary backbone structures for antisense oligonucleotides of the invention include the β-morpholino subunit types shown in FIGS. 4A-4D, each linked by an uncharged, phosphorus-containing subunit linkage. FIG. 4A shows a phosphorus-containing linkage which forms the five atom repeating-unit backbone, where the morpholino rings are linked by a 1-atom phosphoamide linkage. FIG. 4B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 4C:
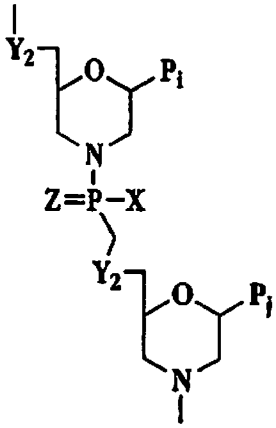
Figure 4D:
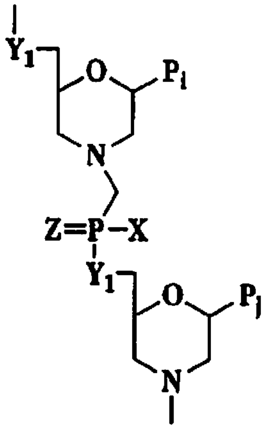

The linkages shown in FIGS. 4C and 4D are designed for 7-atom unit-length backbones. In Structure 4C, the X moiety is as in Structure 4B, and the moiety Y may be methylene, sulfur, or, preferably, oxygen. In Structure 4D, the X and Y moieties are as in Structure 4B. Particularly preferred morpholino oligonucleotides include those composed of morpholino subunit structures of the form shown in FIG. 4B, where $X{=}NH_2$ or $N(CH_3)_2$, $Y{=}O$, and $Z{=}O$.

As noted above, the substantially uncharged oligomer may advantageously include a limited number of charged backbone linkages. One example of a cationic charged phosphordiamidate linkage is shown in FIG. 3H. This linkage, in which the dimethylamino group shown in FIG. 3G is replaced by a 1-piperazino group as shown in FIG. 3G, can be substituted for any linkage(s) in the oligomer. By including between two to eight such cationic linkages, and more generally, at least two and no more than about half the total number of linkages, interspersed along the backbone of the otherwise uncharged oligomer, antisense activity can be enhanced without a significant loss of specificity. The charged linkages are preferably separated in the backbone by at least 1 and preferably 2 or more uncharged linkages.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

V. Inhibition of Viral Replication

The antisense compounds detailed above are useful in inhibiting replication of Nidoviruses in animal cells, including mammalian cells, e.g., human cells, and avian cells. In one embodiment, such inhibition is effective in treating infection of a host animal by these viruses. Accordingly, the method comprises, in one embodiment, contacting a cell infected with the virus with an antisense agent effective to inhibit the replication of the specific virus. In this embodiment, the antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

A. Identification of the Infective Agent

The specific virus causing the infection can be determined by methods known in the art, e.g. serological or cultural methods, or by methods employing the antisense oligomers of the present invention.

Serological identification employs a viral sample or culture isolated from a biological specimen, e.g., stool, urine, cerebrospinal fluid, blood, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Another method for identifying the viral infective agent in an infected subject employs one or more antisense oligomers targeting a spectrum of viral species. Sequences targeting any characteristic viral RNA can be used. The desired target sequences are preferably (i) common to broad virus families/genera, and (ii) not found in the infected host, e.g., humans. Characteristic nucleic acid sequences for a large number of infectious viruses are available in public databases, and may serve as the basis for the design of specific oligomers.

For each plurality of oligomers, the following steps are carried out: (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The virus is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of an antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically accepted carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., ANTISENSE OLIGONUCLEOTIDES: A NEW THERAPEUTIC PRINCIPLE, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. The oligonucleotides may also be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer (PMO), contained in a pharmaceutically acceptable carrier, and is delivered intravenously (IV).

In another application of the method, the subject is a livestock animal, e.g., a chicken, cat, pig, cow or goat, etc., and the treatment is either prophylactic or therapeutic. In other applications, the infected animal to be treated may be a zoo or wild animal, e.g., seal, penguin, or hawk, subject to one or more nidovirus infections. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-25 mg oligomer per 70 kg. In some cases, doses of greater than 25 mg oligomer/patient may be necessary. For IV administration, preferred doses are from about 0.5 mg to 10 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

C. Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al, Antimicrob. Agents and Chemotherapy 39(5):1157-1161, 1995; Anderson, K. P. et al, Antimicrob. Agents and Chemotherapy 40(9):2004-2011, 1996, Cottral, G. E. (ed) in: Manual of Standard Methods for Veterinary Microbiology, pp. 60-93, 1978).

A preferred method of monitoring the efficacy of the antisense oligomer treatment is by detection of the antisense-RNA heteroduplex. At selected time(s) after antisense oligomer administration, a body fluid is collected for detecting the presence and/or measuring the level of heteroduplex species in the sample. Typically, the body fluid sample is collected 3-24 hours after administration, preferably about 6-24 hours after administering. As indicated above, the body fluid sample may be urine, saliva, plasma, blood, spinal fluid, or other liquid sample of biological origin, and may include cells or cell fragments suspended therein, or the liquid medium and its solutes. The amount of sample collected is typically in the 0.1 to 10 ml range, preferably about 1 ml or less.

The sample may be treated to remove unwanted components and/or to treat the heteroduplex species in the sample to remove unwanted ssRNA overhang regions, e.g. by treatment with RNase. It is, of course, particularly important to remove overhang where heteroduplex detection relies on size separation, e.g., electrophoresis of mass spectroscopy.

A variety of methods are available for removing unwanted components from the sample. For example, since the heteroduplex has a net negative charge, electrophoretic or ion exchange techniques can be used to separate the heteroduplex from neutral or positively charged material. The sample may also be contacted with a solid support having a surface-bound antibody or other agent specifically able to bind the heteroduplex. After washing the support to remove unbound material, the heteroduplex can be released in substantially purified form for further analysis, e.g., by electrophoresis, mass spectroscopy or immunoassay.

Materials and Methods

Production of PMO and Peptide Conjugated PMOs

Phosphorodiamidate morpholino oligomers (PMOs) were synthesized at AVI BioPharma (Corvallis, Oreg.) as previously describe (Summerton and Weller 1997). Purity of full length oligomers was >95% as determined by reverse-phase high-pressure liquid chromatography (HPLC) and MALDI TOF mass spectroscopy. To facilitate cellular uptake by in vitro cultured cells, peptide conjugated forms of the PMOs were produced by attaching the carboxy terminal cysteine of the peptide to the 5' end of the PMO through a cross-linker N-[γ-maleimidobutyryloxy] succinimide ester (GMBS) (Moulton and Moulton 2003). The peptide used in this study is designated as P003 ($R_9F_2C$, SEQ ID NO:47). The lyophilized PMOs or peptide-conjugated PMOs were dissolved in sterile $H_2O$ prior to use in cell cultures.

Figure 10:
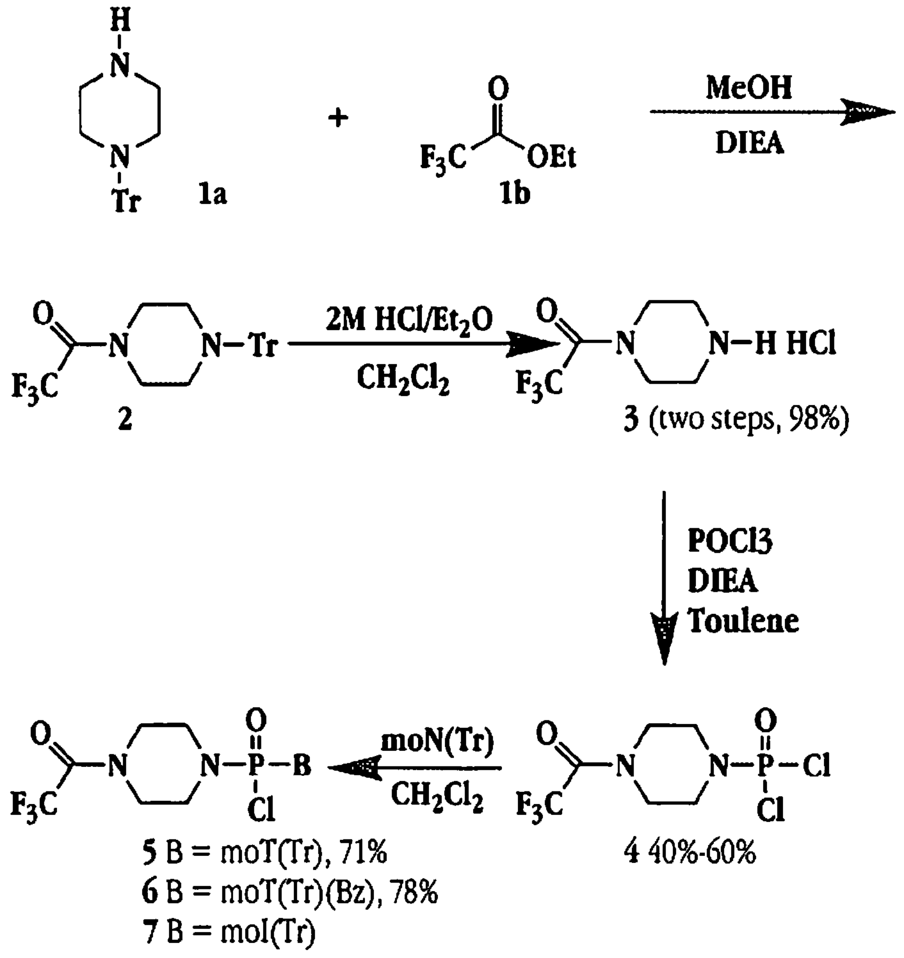
FIG. 10 shows the synthetic steps to produce subunits used to produce +PMO containing the (1-piperazino) phosphinylideneoxy cationic linkage as shown in FIG. 3H.

A schematic of a synthetic pathway that can be used to make morpholino subunits containing a (1 piperazino) phosphinylideneoxy linkage is shown in FIG. 10; further experimental detail for a representative synthesis is provided in Materials and Methods, below. As shown in the Figure, reaction of piperazine and trityl chloride gave trityl piperazine (1a), which was isolated as the succinate salt. Reaction with ethyl trifluoroacetate (1b) in the presence of a weak base (such as diisopropylethylamine or DIEA) provided 1-trifluoroacetyl-4-trityl piperazine (2), which was immediately reacted with HCl to provide the salt (3) in good yield. Introduction of the dichlorophosphoryl moiety was performed with phosphorus oxychloride in toluene.

The acid chloride (4) is reacted with morpholino subunits (moN), which may be prepared as described in U.S. Pat. No. 5,185,444 or in Summerton and Weller, 1997 (cited above), to provide the activated subunits (5,6,7). Suitable protecting groups are used for the nucleoside bases, where necessary; for example, benzoyl for adenine and cytosine, isobutyryl for guanine, and pivaloylmethyl for inosine. The subunits containing the (1 piperazino) phosphinylideneoxy linkage can be incorporated into the existing PMO synthesis protocol, as described, for example in Summerton and Weller (1997), without modification.

EXAMPLES

Example 1

Antisense PMO Reduction of SARS Virus and MHV Titer in Vitro

Figure 9:
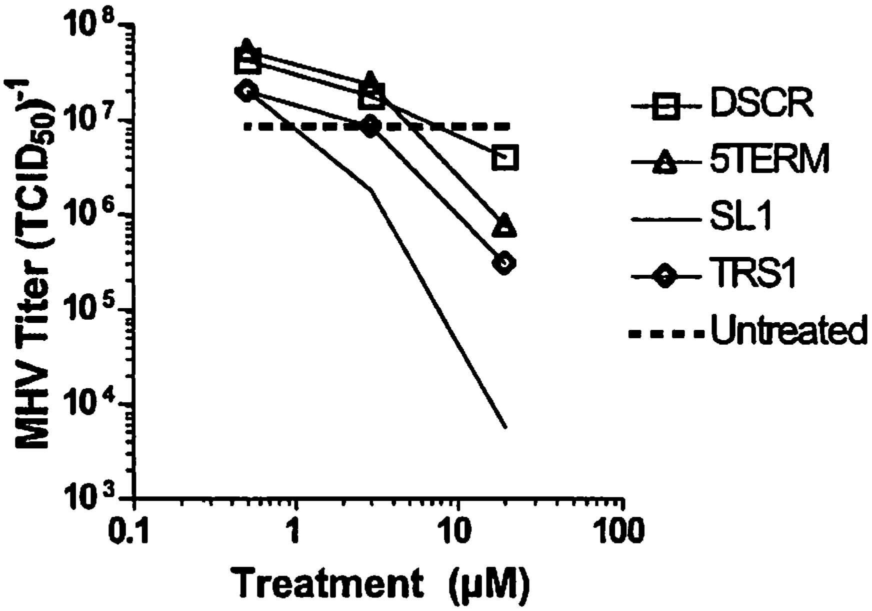
FIG. 9 shows graphically the reduction of MHV viral titer when MHV-infected cells are cultured in the presence of a PMO targeted to the leader TRS of MHV.

The capability of an antiviral drug to reduce the production of viable virus is a classic measure of antiviral drug activity. The reduction of SARS virus titer produced from SARS-infected Vero-E6 cells cultured in the presence of anti-leader TRS PMO (SEQ ID NOS:26 and 27) was measured and the results shown in FIG. 5. The reduction of MHV titer when MHV-infected Vero-E6 cells were cultured in the presence of a PMO that targets the leader TRS (SEQ ID NO:29) was also determined and is shown in FIG. 9.

Vero-E6 cells were cultured in DMEM with 10% fetal bovine serum. Vero-E6 cells were plated at approximately 75% confluence in replicate 25 $cm^2$ culture flasks. Cells were rinsed and incubated in 1 ml of complete VP-SFM (virus production serum-free medium, Invitrogen) containing the specified concentration of antisense PMO-P003 conjugate (SEQ ID NOS: 26 or 27) or a PMO-P003 conjugate with an irrelevant sequence (DSscr) for 12-16 h (overnight). Cells were transferred to the BSL-3 containment facility at this point and inoculated with SARS-CoV at a multiplicity of approximately 0.1 PFU/cell by adding virus directly to the treatment medium for 1 h at 37 C and in the presence of 5% $CO_2$. Other multiplicities were tested in some experiments and drug effects were not found to differ. After 1 h adsorbtion, 4 ml of VP-SFM was added and cells were incubated for 24 h. Virus-containing supernatants were collected and stored at −80 C until titration. Titration was by standard Vero-E6 plaque assay. Wells containing approximately 75% confluent Vero-E6 cells were inoculated with serial dilutions of virus, incubated 1 h at 37 C in the presence of 5% $CO_2$ and then overlaid with 0.7% agarose in 1×DMEM. Cells were incubated 72 h, fixed by immersion of the plate in 10% formalin saline for 24 h, surface decontaminated with 95% ethanol and removed from the BSL-3 facility. Plaques were visualized with 0.1% crystal violet and counted. Virus titer is calculated and presented in FIG. 5 as mean+/−SEM. From the data presented in FIG. 5, it is clear that anti-leader TRS PMOs reduce the viral titer produced from SARS-infected Vero-E6 cells.

The same method was used to determine the antiviral activity of a P003-PMO conjugate (SEQ ID NO:47 conjugated to SEQ ID NO:29) targeted to the TRS leader sequence of MHV. A reduced viral titer was observed as shown in FIG. 9. In FIG. 9, the data for TRS1 refers to the P003 conjugated PMO (SEQ ID NO:29). The figure indicates an approximately two-log reduction in viral titer in the presence of the TRS1 PMO.

Example 2

Antisense PMO Reduction of SARS Plaque Size

As a separate measure of the antiviral activity of antisense PMO drugs, the anti-leader TRS PMOs were used to measure the reduction of viral replication in a plaque size assay. As viral replication is inhibited a corresponding reduction in the spread of cytopathic effects is observed as a reduction in plaque size. Furthermore, since virus entry and spread are separable phenomena with different criteria, and since some reports indicate that the antisense PMO drugs may inhibit initial virus entry, the plaque size reduction assay is performed. This assay also tests the non-toxicity of drug over longer treatment periods.

Figure 5:
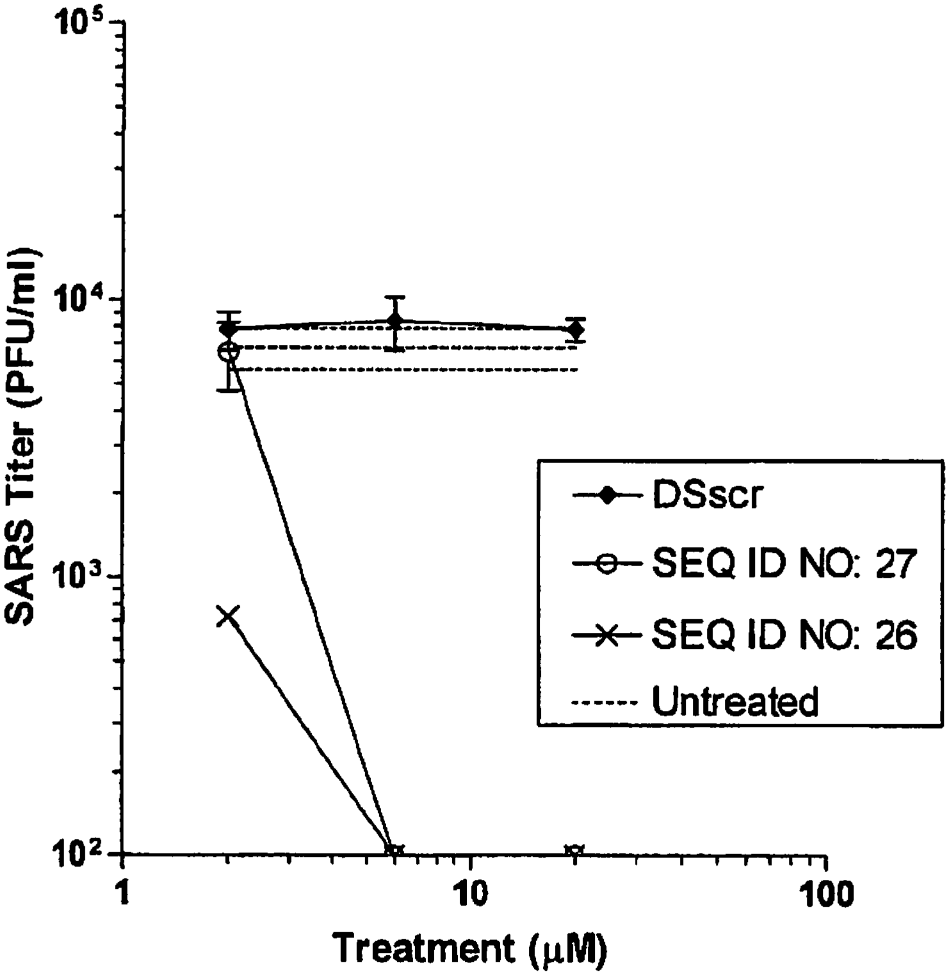
FIG. 5 shows graphically the reduction of SARS viral titer when SARS-infected cells are cultured in the presence of either of two antisense PMOs targeted at the leader transcriptional regulatory sequence.

As described above in Example 1, 75% confluent Vero-E6 cells were prepared in plates but not pretreated. Cells were transported to the BSL-3 facility, inoculated with serial dilutions of SARS virus calculated to produce 1, 10 and 100 plaques per plate. The same serial dilution stocks were used for all control and test plate inoculations. After 1 h adsorbtion of inoculum, cells were overlaid with 0.7% agarose in 0.25× PBS, 0.75×VP-SFM to make an isotonic nutrient overlay. Each overlay was made separately with PMO-P003 conjugate (SEQ ID NOS: 26 and 27) added to the molten agarose/VP-SFM preparation immediately prior to overlay. Overlay volume is 2 ml and drug is added to make this volume up to the desired concentration. Cells are incubated at 37 C in the presence of 5% $CO_2$ for 72 h, then fixed, decontaminated and stained as described in Example 1. Plaque diameter was measured for all visible plaques to the nearest 0.5 mm using a ruler. Where fewer pinprick plaques than expected are present at effective concentrations of drug, zero-diameter plaques are recorded to make up the expected titer, based on untreated controls. This is valid since virus binding and entry have been completed prior to differentiation of plates by addition of treatment-overlay. Plaque size was plotted (mean+/−SEM) for approximately equal numbers of plaques from replicate wells as shown in FIG. 5. From the data in FIG. 6, it is clear that both anti-leader TRS PMOs, SEQ ID NOS: 26 and 27 are highly effective at reducing the plaque size of SARS-infected Vero-E6 cells.

Example 3

Antisense PMO Reduction of SARS Cytopathic Effects in Vitro

Figure 6:
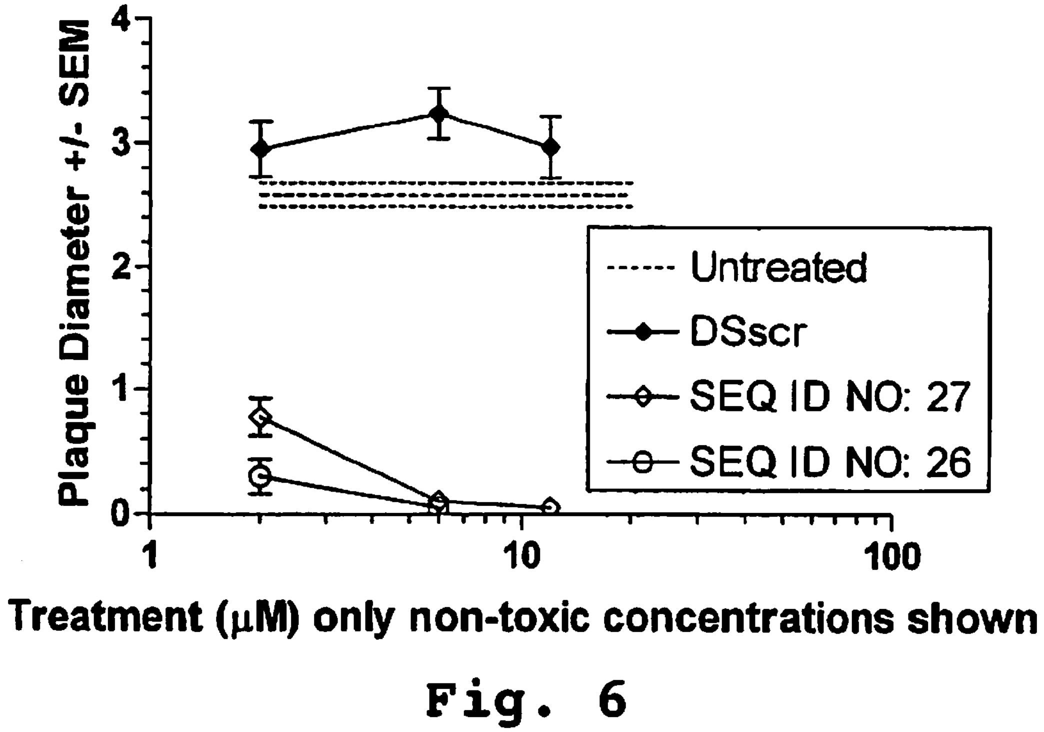
FIG. 6 shows graphically the reduction in SARS plaque size when infected cells are cultured in the presence of either of two antisense PMOs targeted at the leader transcriptional regulatory sequence.
Figure 7A:
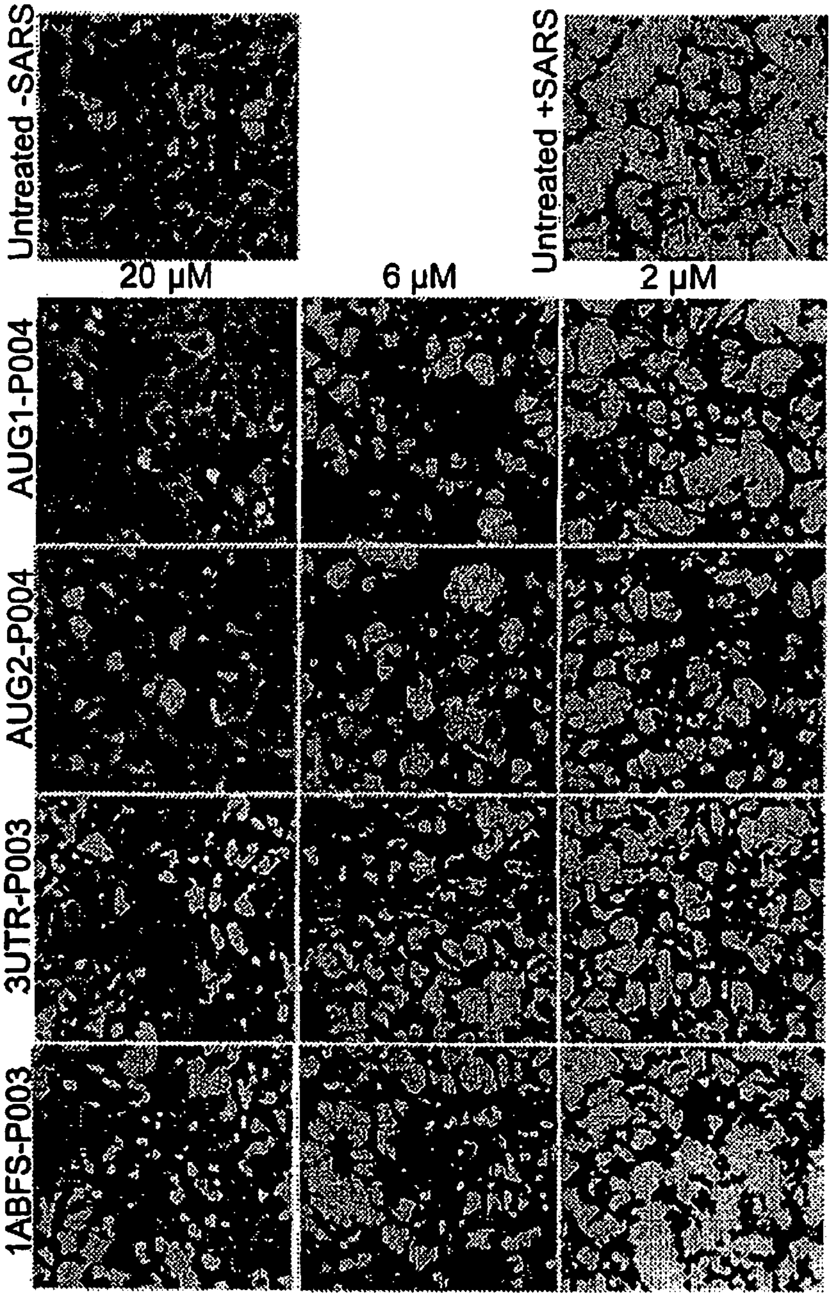
FIGS. 7A and 7B show photomicrographs of SARS-infected cells, control cells and the corresponding SARS-induced cytopathic effects in the presence of a variety of antisense PMO compounds including two antisense PMOs targeted at the leader transcriptional regulatory sequence.
Figure 7B:
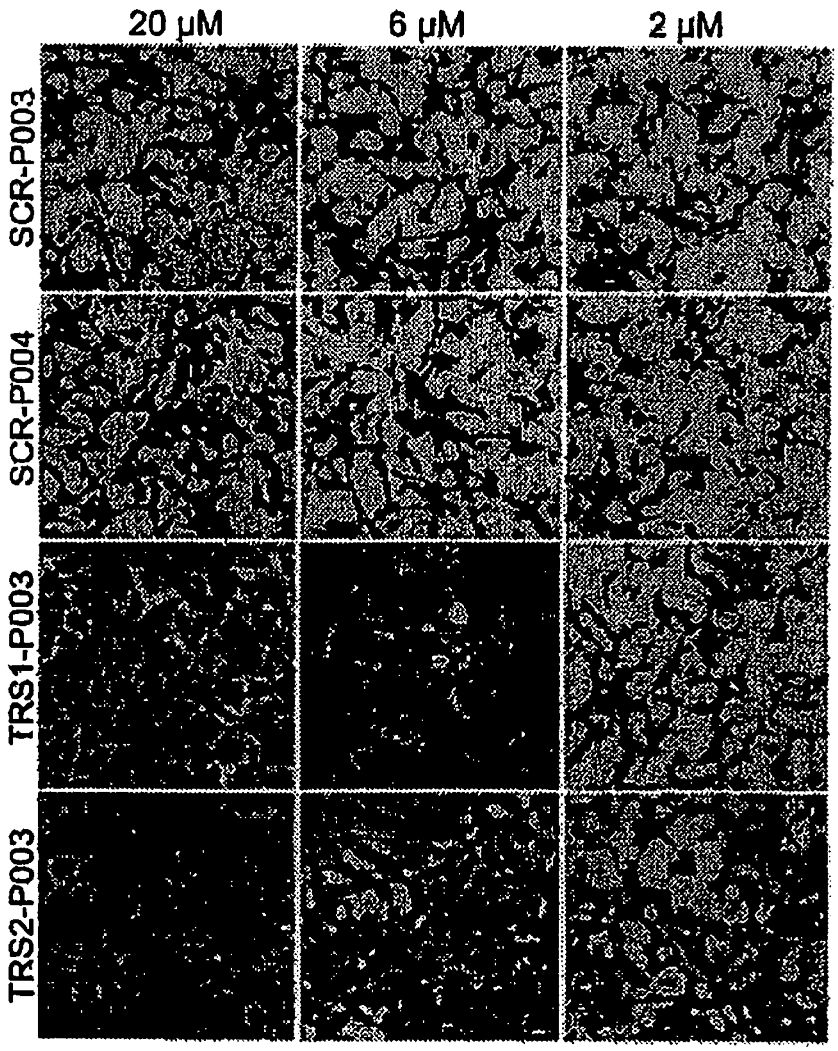

This assay is a byproduct of the virus titer reduction assay. The observation of cytopathic effects (CPE) is a visual measure of antiviral drug activity. Vero-E6 cells were pretreated, inoculated with SARS virus and cultured as above in the presence of anti-leader TRS PMOs (SEQ ID NOS: 26 & 27). After 24 h, the medium was replaced by fresh complete VP-SFM and cells were incubated a further 24 h at 37 C in the presence of 5% $CO_2$. 48 h after inoculation, the cells were fixed, decontaminated and stained with crystal violet as described in Example 1. CPE is visualized by phase contrast microscopy and recorded with a digital camera as shown in FIG. 6. The data for TRS-1-P003 and TRS-2-P003 correspond to SEQ ID NOS: 26 and 27, respectively. The other treatments presented in FIG. 7 are not relevant to the present invention. From the data presented in FIG. 7, it is clear that anti-leader TRS PMO prevented SARS-induced CPE at concentrations as low as 2 micromolar, (e.g. SEQ ID NO: 27 or TRS2-P003).

Example 4

Antisense PMO Reduction of Equine Arteritis Virus Replication in Vitro

Figure 8A:
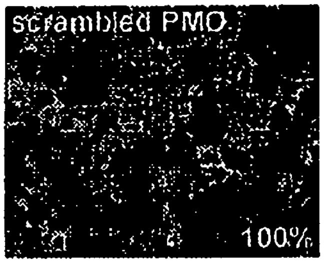
FIGS. 8A-8C show photomicrographs of EAV-infected cells, control cells and the corresponding immunofluorescence using labeled antibodies to EAV-specific proteins in the presence of an antisense PMO that targets the leader TRS of EAV.
Figure 8B:
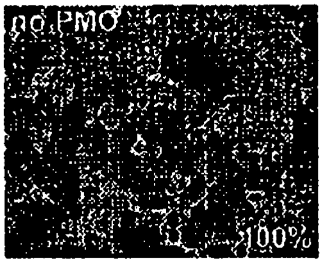
Figure 8C:
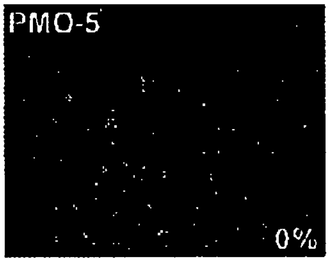

Equine arteritis virus (EAV) is an enveloped plus-strand RNA virus of the family Arteriviridae (order Nidovirales) that causes respiratory and reproductive disease in equids. EAV is the prototype virus for the Arteriviridae family and has been studied extensively at the molecular level (Ziebuhr, Snijder et al. 2000; Pasternak, van den Born et al. 2001; Pasternak, van den Born et al. 2003; Balasuriya, Hedges et al. 2004; Pasternak, Spaan et al. 2004; VAN DEN BORN, GULTYAEV et al. 2004). An anti-leader TRS PMO (SEQ ID NO:46) was used to treat EAV-infected cell cultures and antiviral activity was measured using immunofluorescence as shown in FIG. 8 and described below.

Vero E6 cells were treated with $R_9F_2C$-conjugated PMO (SEQ ID NO:47 conjugated to SEQ ID NO:46) for six hours in culture medium lacking fetal calf serum. After PMO pretreatment, cells were inoculated with EAV at an M.O.I. of 0.5 for one hour. Medium containing 8% serum and no PMO was then added back and the cultures incubated at 37° C. for 24 hours. An immunofluorescence assay (IFA) using two different EAV-specific antibody-fluorescent dye combinations was performed on the cells and the photomicrographs are shown in FIG. 8. The fluorescent antibodies are specific for the nsp3 and N proteins of EAV. FIG. 8 shows the antiviral effect of the anti-leader TRS PMO (PMO-5, SEQ ID NO:46) compared to a scrambled control PMO and no PMO treatment. The percent figure in the lower right corner of each photomicrograph indicates the relative virus-specific immunofluorescence for that sample. In addition, different concentrations of PMO were used to determine an approximate $IC_{50}$ value using the. Based on these assays the EAV-specific anti-leader TRS PMO (SEQ ID NO:46) produced an $IC_{50}$ of 2.5 μM.

Sequence Listing

| Sequence (5' to 3') | SEQ ID NO |
|---|---|
| cggacaccaacucga**acuaaac**gaaau | 1 |
| cggacaccaacucga**acuaaac**gaaau | 2 |
| cuacuuuucuca**acuaaac**gaaau | 3 |
| gaucuuuuuguaa**ucuaaac**uuua | 4 |
| gaucuguucucuaa**acgaac**uuua | 5 |
| guaguuuaaaucu**aaucuaaac**uuua | 6 |
| gauuugcagacccucc**uuaacc**auguuc | 7 |
| cggucucuccaccccuu**uaacc**auguc | 8 |
| caucgucgucgaucucua**ucaacu**accc | 9 |
| aaaauaaacau**guucgu**uuag | 10 |
| acaaauccauaa**guucgu**uua | 11 |
| cgaaugaguacauaa**guucgu** | 12 |
| auaauaguua**guucgu**uuaga | 13 |
| uuguaauaagaaagc**guucgu** | 14 |
| gaauaauuuucau**guucgu**uu | 15 |
| gaaguuucau**guucgu**uuaga | 16 |
| acauuuuaauuu**guucgu**uua | 17 |
| ucagcacgucgucgu**gguuga** | 18 |
| agccauacuuccuca**gguuaa** | 19 |
| atttcgtttagttcgagttgg | 20 |
| gtttagttcgagttggtgtccg | 21 |
| atttcgtttagttgagaaaag | 22 |
| gtttagttgagaaaagtag | 23 |
| taaagtttagattacaaaaag | 24 |
| gtttagattacaaaaagatc | 25 |
| taaagttcgtttagagaacag | 26 |
| gttcgtttagagaacagatc | 27 |
| taaagtttagattagatttaaac | 28 |
| gtttagattagatttaaactac | 29 |
| gaacatggttaaggagggtctg | 30 |
| ggttaaggagggtctgcaaatc | 31 |
| gacatggttaaaggggtggag | 32 |
| ggttaaaggggtggagagaccg | 33 |

-continued

| Sequence Listing | |
|---|---|
| Sequence (5' to 3') | SEQ ID NO |
| gggtagttgatagagatcgacg | 34 |
| agttgatagagatcgacgacgatg | 35 |
| ctaaacgaacatgtttatttt | 36 |
| taaacgaacttatggatttgt | 37 |
| acgaacttatgtactcattcg | 38 |
| tctaaacgaactaactattat | 39 |
| acgaacgctttcttattacaa | 40 |

-continued

| Sequence Listing | |
|---|---|
| Sequence (5' to 3') | SEQ ID NO |
| aaacgaacatgaaaattattc | 41 |
| tctaaacgaacatgaaacttc | 42 |
| taaacgaacaaattaaaatgt | 43 |
| tcaaccacgacgacgtgctga | 44 |
| ttaacctgaggaagtatggct | 45 |
| ccatagtcgcaagggtagttga | 46 |
| $nh_2$-rrrrrrrrrffc-$co_2$h | 47 |

It is claimed:

1. An antisense compound, which is composed of morpholino subunits and phosphorus-containing intersubunit linkages, which join a morpholino nitrogen of one subunit to a 5' exocyclic carbon of an adjacent subunit, for use in inhibiting replication of a nidovirus in mammalian host cells, comprising:

(i) a nuclease-resistant backbone, (ii) 12-25 nucleotide bases, and (iii) a targeting sequence that is complementary to at least 12 contiguous bases contained in SEQ ID NO: 3;

wherein the targeting sequence forms a heteroduplex structure composed of SEQ ID NO: 3 and the antisense compound, SEQ ID NO:3 comprising a transcriptional regulatory sequence in a 5' leader region of a positive-strand viral genome, the heteroduplex structure characterized by a $T_m$, of dissociation of at least 45° C., wherein the heteroduplex structure disrupts base pairing between the transcriptional regulatory sequence in the 5' leader region of the positive-strand viral genome and a negative-strand 3' subgenomic region, thereby inhibiting viral replication.

2. The compound of claim 1, in which at least 2 and no more than half of the total number of intersubunit linkages are cationic linkages.

3. The compound of claim 2, wherein said morpholino subunits are joined by phosphorodiamidate linkages, in accordance with the structure:

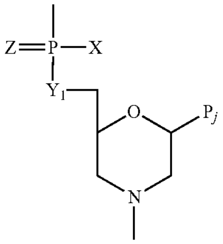

where $Y_1$=O, Z=O, Pj is a purine or pyrimidine base-pairing moiety effective to bind, by base-specific hydrogen bonding, to a base in a polynucleotide, and X for the uncharged linkages is alkyl, alkoxy, thioalkoxy, or an alkyl amino of the form wherein $NR_2$, where each R is independently hydrogen or methyl, and for the positively charged linkages, X is 1-piperazine.

4. The compound of claim 1, which contains a sequence selected from the group consisting of SEQ ID NOS: 22 and 23.

5. The compound of claim 1, wherein the compound is conjugated to an Arg-rich peptide.

6. The compound of claim 5, wherein the peptide is SEQ ID NO: 47.

7. The compound of claim 1, in which the intersubunit linkages are uncharged.

8. The compound of claim 7, wherein the morpholino subunits are joined by phosphorodiamidate linkages, in accordance with the structure:

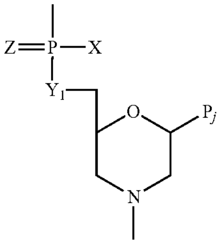

where $Y_1$=O, Z=O, Pj is a purine or pyrimidine base pairing moiety effective to bind, by base-specific hydrogen bonding, to a base in a polynucleotide, and X is alkyl, alkoxy, thioalkoxy, amino or alkyl amino, including dialkylamino.

* * * * *

UNITED STATES PATENT AND TRADEMARK OFFICE

CERTIFICATE OF CORRECTION

PATENT NO. : 8,759,307 B2
APPLICATION NO. : 12/109856
DATED : June 24, 2014
INVENTOR(S) : Stein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1247 days.

Signed and Sealed this
Eighth Day of September, 2015

Michelle K. Lee
*Director of the United States Patent and Trademark Office*

SEQUENCE LISTING

<160> NUMBER OF SEQ ID NOS: 47

<210> SEQ ID NO 1
<211> LENGTH: 27
<212> TYPE: RNA
<213> ORGANISM: Feline coronavirus

<400> SEQUENCE: 1
cggacaccaa cucgaacuaa acgaaau 27

<210> SEQ ID NO 2
<211> LENGTH: 27
<212> TYPE: RNA
<213> ORGANISM: Transmissible gastroenteritis virus

<400> SEQUENCE: 2
cggacaccaa cucgaacuaa acgaaau 27

<210> SEQ ID NO 3
<211> LENGTH: 24
<212> TYPE: RNA
<213> ORGANISM: Human coronavirus 229E

<400> SEQUENCE: 3
cuacuuuucu caacuaaacg aaau 24

<210> SEQ ID NO 4
<211> LENGTH: 24
<212> TYPE: RNA
<213> ORGANISM: Human coronavirus OC43

<400> SEQUENCE: 4
gaucuuuuug uaaucuaaac uuua 24

<210> SEQ ID NO 5
<211> LENGTH: 24
<212> TYPE: RNA
<213> ORGANISM: Severe acute respiratory syndrome coronavirus

<400> SEQUENCE: 5
gaucuguucu cuaaacgaac uuua 24

<210> SEQ ID NO 6
<211> LENGTH: 26
<212> TYPE: RNA

-continued

<213> ORGANISM: Murine hepatitis virus

<400> SEQUENCE: 6
guaguuuaaa ucuaaucuaa acuuua 26

<210> SEQ ID NO 7
<211> LENGTH: 28
<212> TYPE: RNA
<213> ORGANISM: Simian hemorrhagic fever virus

<400> SEQUENCE: 7
gauuugcaga cccuccuuaa ccauguuc 28

<210> SEQ ID NO 8
<211> LENGTH: 27
<212> TYPE: RNA
<213> ORGANISM: Porcine reproductive and respiratory syndrome virus

<400> SEQUENCE: 8
cggucucucc accccuuuaa ccauguc 27

<210> SEQ ID NO 9
<211> LENGTH: 28
<212> TYPE: RNA
<213> ORGANISM: Equine arteritis virus

<400> SEQUENCE: 9
caucgucguc gaucucuauc aacuaccc 28

<210> SEQ ID NO 10
<211> LENGTH: 21
<212> TYPE: RNA
<213> ORGANISM: Severe acute respiratory syndrome coronavirus

<400> SEQUENCE: 10
aaaauaaaca uguucguuua g 21

<210> SEQ ID NO 11
<211> LENGTH: 21
<212> TYPE: RNA
<213> ORGANISM: Severe acute respiratory syndrome coronavirus

<400> SEQUENCE: 11
acaaauccau aaguucguuu a 21

<210> SEQ ID NO 12
<211> LENGTH: 21
<212> TYPE: RNA
<213> ORGANISM: Severe acute respiratory syndrome coronavirus

<400> SEQUENCE: 12
cgaaugagua cauaaguucg u 21

<210> SEQ ID NO 13
<211> LENGTH: 21
<212> TYPE: RNA
<213> ORGANISM: Severe acute respiratory syndrome coronavirus

<400> SEQUENCE: 13
auaauaguua guucguuuag a 21

<210> SEQ ID NO 14
<211> LENGTH: 21

-continued

<212> TYPE: RNA
<213> ORGANISM: Severe acute respiratory syndrome coronavirus

<400> SEQUENCE: 14
uuguaauaag aaagcguucg u 21

<210> SEQ ID NO 15
<211> LENGTH: 21
<212> TYPE: RNA
<213> ORGANISM: Severe acute respiratory syndrome coronavirus

<400> SEQUENCE: 15
gaauaauuuu cauguucguu u 21

<210> SEQ ID NO 16
<211> LENGTH: 21
<212> TYPE: RNA
<213> ORGANISM: Severe acute respiratory syndrome coronavirus

<400> SEQUENCE: 16
gaaguuucau guucguuuag a 21

<210> SEQ ID NO 17
<211> LENGTH: 21
<212> TYPE: RNA
<213> ORGANISM: Severe acute respiratory syndrome coronavirus

<400> SEQUENCE: 17
acauuuuaau uuguucguuu a 21

<210> SEQ ID NO 18
<211> LENGTH: 21
<212> TYPE: RNA
<213> ORGANISM: Simian hemorrhagic fever virus

<400> SEQUENCE: 18
ucagcacguc gucgugguug a 21

<210> SEQ ID NO 19
<211> LENGTH: 21
<212> TYPE: RNA
<213> ORGANISM: Simian hemorrhagic fever virus

<400> SEQUENCE: 19
agccauacuu ccucagguua a 21

<210> SEQ ID NO 20
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 20
atttcgttta gttcgagttg g 21

<210> SEQ ID NO 21
<211> LENGTH: 22
<212> TYPE: DNA
<213> ORGANISM: Artificial sequence
<220> FEATURE:
<223> OTHER INFORMATION: synthetic antisense oligonucleotide

<400> SEQUENCE: 21

-continued

```
gtttagttcg agttggtgtc cg                                                22


<210> SEQ ID NO 22
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 22

atttcgttta gttgagaaaa g                                                 21


<210> SEQ ID NO 23
<211> LENGTH: 19
<212> TYPE: DNA
<213> ORGANISM: Artificial sequence
<220> FEATURE:
<223> OTHER INFORMATION: synthetic antisense oligonucleotide

<400> SEQUENCE: 23

gtttagttga gaaaagtag                                                    19


<210> SEQ ID NO 24
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 24

taaagtttag attacaaaaa g                                                 21


<210> SEQ ID NO 25
<211> LENGTH: 20
<212> TYPE: DNA
<213> ORGANISM: Artificial sequence
<220> FEATURE:
<223> OTHER INFORMATION: synthetic antisense oligonucleotide

<400> SEQUENCE: 25

gtttagatta caaaaagatc                                                   20


<210> SEQ ID NO 26
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 26

taaagttcgt ttagagaaca g                                                 21


<210> SEQ ID NO 27
<211> LENGTH: 20
<212> TYPE: DNA
<213> ORGANISM: Artificial sequence
<220> FEATURE:
<223> OTHER INFORMATION: synthetic antisense oligonucleotide

<400> SEQUENCE: 27

gttcgtttag agaacagatc                                                   20


<210> SEQ ID NO 28
<211> LENGTH: 23
<212> TYPE: DNA
<213> ORGANISM: Artificial sequence
```

-continued

<220> FEATURE:
<223> OTHER INFORMATION: synthetic antisense oligonucleotide

<400> SEQUENCE: 28
taaagtttag attagattta aac 23

<210> SEQ ID NO 29
<211> LENGTH: 22
<212> TYPE: DNA
<213> ORGANISM: Artificial sequence
<220> FEATURE:
<223> OTHER INFORMATION: synthetic antisense oligonucleotide

<400> SEQUENCE: 29
gtttagatta gatttaaact ac 22

<210> SEQ ID NO 30
<211> LENGTH: 22
<212> TYPE: DNA
<213> ORGANISM: Artificial sequence
<220> FEATURE:
<223> OTHER INFORMATION: synthetic antisense oligonucleotide

<400> SEQUENCE: 30
gaacatggtt aaggagggtc tg 22

<210> SEQ ID NO 31
<211> LENGTH: 22
<212> TYPE: DNA
<213> ORGANISM: Artificial sequence
<220> FEATURE:
<223> OTHER INFORMATION: synthetic antisense oligonucleotide

<400> SEQUENCE: 31
ggttaaggag ggtctgcaaa tc 22

<210> SEQ ID NO 32
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 32
gacatggtta aaggggtgga g 21

<210> SEQ ID NO 33
<211> LENGTH: 22
<212> TYPE: DNA
<213> ORGANISM: Artificial sequence
<220> FEATURE:
<223> OTHER INFORMATION: synthetic antisense oligonucleotide

<400> SEQUENCE: 33
ggttaaaggg gtggagagac cg 22

<210> SEQ ID NO 34
<211> LENGTH: 22
<212> TYPE: DNA
<213> ORGANISM: Artificial sequence
<220> FEATURE:
<223> OTHER INFORMATION: synthetic antisense oligonucleotide

<400> SEQUENCE: 34
gggtagttga tagagatcga cg 22

-continued

<210> SEQ ID NO 35
<211> LENGTH: 24
<212> TYPE: DNA
<213> ORGANISM: Artificial sequence
<220> FEATURE:
<223> OTHER INFORMATION: synthetic antisense oligonucleotide

<400> SEQUENCE: 35
agttgataga gatcgacgac gatg 24

<210> SEQ ID NO 36
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 36
ctaaacgaac atgtttattt t 21

<210> SEQ ID NO 37
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 37
taaacgaact tatggatttg t 21

<210> SEQ ID NO 38
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 38
acgaacttat gtactcattc g 21

<210> SEQ ID NO 39
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 39
tctaaacgaa ctaactatta t 21

<210> SEQ ID NO 40
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 40
acgaacgctt tcttattaca a 21

<210> SEQ ID NO 41
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 41
aaacgaacat gaaaattatt c 21

<210> SEQ ID NO 42
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 42
tctaaacgaa catgaaactt c 21

<210> SEQ ID NO 43
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 43
taaacgaaca aattaaaatg t 21

<210> SEQ ID NO 44
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 44
tcaaccacga cgacgtgctg a 21

<210> SEQ ID NO 45
<211> LENGTH: 21
<212> TYPE: DNA
<213> ORGANISM: Artificial sequence
<220> FEATURE:
<223> OTHER INFORMATION: synthetic antisense oligonucleotide

<400> SEQUENCE: 45
ttaacctgag gaagtatggc t 21

<210> SEQ ID NO 46
<211> LENGTH: 22
<212> TYPE: DNA
<213> ORGANISM: Artificial sequence
<220> FEATURE:
<223> OTHER INFORMATION: synthetic antisense oligonucleotide

<400> SEQUENCE: 46
ccatagtcgc aagggtagtt ga 22

<210> SEQ ID NO 47
<211> LENGTH: 12
<212> TYPE: PRT
<213> ORGANISM: Artificial Sequence
<220> FEATURE:
<223> OTHER INFORMATION: synthetic Arginine-rich peptide

<400> SEQUENCE: 47

Arg Arg Arg Arg Arg Arg Arg Arg Arg Phe Phe Cys
1 5 10